(12) United States Patent
Barth et al.

(10) Patent No.: US 6,979,683 B2
(45) Date of Patent: Dec. 27, 2005

(54) BENZIMIDAZOLE DERIVATIVES, PREPARATION AND THERAPEUTIC USE THEREOF

(75) Inventors: Francis Barth, Saint Georges d'Orques (FR); Daniel Bichon, Montpellier (FR); Frank Bolkenius, Kehl (DE); Viviane Van Dorsselaer, Strasbourg (FR)

(73) Assignee: Sanofi-Synthelabo, Paris (FR)

( * ) Notice: Subject to any disclaimer, the term of this patent is extended or adjusted under 35 U.S.C. 154(b) by 107 days.

(21) Appl. No.: 10/432,672

(22) PCT Filed: Nov. 21, 2001

(86) PCT No.: PCT/FR01/03667

§ 371 (c)(1), (2), (4) Date: May 23, 2003

(87) PCT Pub. No.: WO02/42306

PCT Pub. Date: May 30, 2002

(65) Prior Publication Data

US 2004/0029866 A1 Feb. 12, 2004

(30) Foreign Application Priority Data

Nov. 23, 2000 (FR) .............................. 00 15141
May 10, 2001 (FR) .............................. 01 06157

(51) Int. Cl.$^7$ ................... C07D 487/06; A61K 31/5517
(52) U.S. Cl. ........................ 514/220; 540/498
(58) Field of Search .................. 514/220; 540/220, 540/498

(56) References Cited

U.S. PATENT DOCUMENTS

| 5,589,476 A | 12/1996 | Jegham et al. |
| 6,448,271 B1 | 9/2002 | Lubisch et al. |
| 6,548,494 B1 * | 4/2003 | Webber et al. ............... 514/220 |

FOREIGN PATENT DOCUMENTS

| CA | 2171579 | 9/1996 |
| EP | 0 732 334 | 9/1986 |
| EP | 0 646 583 | 4/1995 |
| WO | WO 00/32579 | 6/2000 |

OTHER PUBLICATIONS

Emanuela Mazzon et al., "GPI 6150, a poly (ADP–ribose) polymerase inhibitor, exhibits an anti– inflammatory effect in rat models of inflammation," *European Journal of Pharmacology* 415:85–94 (2001).

Andrew A. Pieper et al., "Poly (ADP–ribose) polymerase, nitric oxide and cell death," *Trends in Pharmaceutical Sciences* 20:171–181 (1999).
Csaba Szabó et al., "Role of poly(ADP–ribose) synthetase in inflammation and ischaemia– reperfusion," *Trends in Pharmaceutical Sciences* 19:287–298 (1998).
Derwent abstract for EP 0 646 583, dated Apr. 5, 1995.
Derwent abstract for EP 0 732 334, dated Sep. 18, 1886.
Derwent abstract for WO 00/32579, dated Jun. 8, 2000.

* cited by examiner

Primary Examiner—Bruck Kifle
(74) Attorney, Agent, or Firm—Finnegan, Henderson, Farabow, Garrett & Dunner, L.L.P.

(57) ABSTRACT

The invention relates to benzimidazole derivatives of general formula (I)

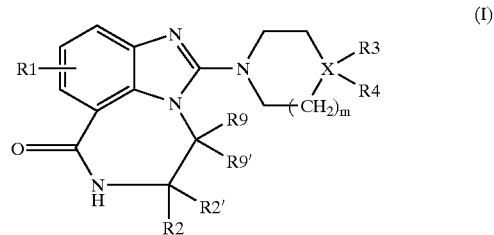

in which
X represents a nitrogen atom or a carbon atom;
and when X represents a nitrogen atom
R3 represents in particular a hydrogen atom or a (C1–C4) alkyl group,
R4 represents in particular a hydrogen atom; a (C1–C6) alkyl; (C3–C7)cycloalkyl; 4-piperidyl; —(CH$_2$)$_p$—NR5R6; —(CH$_2$)$_p$—CONR5R6; —CO—(CH$_2$)$_p$—NR5R6; —(CH$_2$)$_p$-phenyl; —(CH$_2$)$_p$-morpholinyl; —(CH$_2$)$_p$-pyrrolidinyl; —(CH$_2$)$_p$-tetrahydroisoquinoline; —(CH$_2$)$_p$-heteroaryl; heteroarylcarbonyl; phenylcarbonyl; (C1–C6) alkylcarbonyl; —(CH$_2$)$_p$—COOR'; or phenylsulphonyl group;
and when X represents a carbon atom
R3 represents a hydrogen atom; a group —NR5R6; —NHCOR7; —CONHR5; —COR7; —NHCONH$_2$; —OH or —CH$_2$OH,
R4 represents in particular a hydrogen atom; an optionally substituted group —(CH$_2$)$_p$-phenyl; a group —(CH$_2$)$_p$-heteroaryl; or a group —(CH$_2$)$_t$NR7R8.

Preparation process and therapeutic application.

13 Claims, No Drawings

BENZIMIDAZOLE DERIVATIVES, PREPARATION AND THERAPEUTIC USE THEREOF

This application is a national stage filing under 35 U.S.C. § 371 of international application no. PCT/FR01/03667, filed on Nov. 21, 2001. This application claims the benefit of priority under 35 U.S.C. § 119(a) to French patent application no. 00/15141, filed on Nov. 23, 2000, and French patent application no. 01/06157, filed on May 10, 2001.

The present invention relates to benzimidazole derivatives, to their preparation and to their therapeutic application.

One subject of the present invention is compounds corresponding to formula (I)

(I)

in which

R1 represents a hydrogen atom, a (C1–C4)alkyl group, a halogen atom, a nitro group or a (C1–C4)alkoxy group, R2, R2', R9 and R9' represent, independently of each other, a hydrogen atom or a (C1–C4)alkyl group, X represents a nitrogen atom or a carbon atom, m is equal to 1 or 2, and when X represents a nitrogen atom:

R3 represents a hydrogen atom or a (C1–C4)alkyl group to give compounds of formula (I) comprising a quaternary ammonium, or alternatively it does not exist, to give compounds of formula (I) comprising a secondary or tertiary amine, R4 represents:
a hydrogen atom,
a (C1–C6)alkyl group,
a (C3–C7)cycloalkyl group,
a 4-piperidyl group optionally substituted on a carbon atom or on the nitrogen atom with a (C1–C4)alkyl group,
a group —(CH$_2$)$_p$—NR5R6, —(CH$_2$)$_p$—CONR5R6 or —CO—(CH$_2$)$_p$—NR5R6, in which p may range from 0 to 4 and in which R5 and R6 represent, independently of each other, a hydrogen atom or a (C1–C4)alkyl group,
a group —(CH$_2$)$_p$-phenyl, in which p may range from 0 to 4 (for example a benzyl group when p=1 or a phenylethyl group when p=2) and in which the phenyl nucleus is optionally substituted with one to three groups chosen, independently of each other, from: a (C1–C4)alkyl group, a nitro group, a hydroxyl group, an amino group, a halogen atom, a trifluoromethyl group, a (C1–C4)alkoxy group, a (C1–C4)alkylamino group, a (C1–C4)dialkylamino group, an —NHCHO group, a group —NHCOR or a group —NHSO$_2$R, in which R represents a (C1–C4)alkoxy group or a (C1–C4)alkyl group, this (C1–C4)alkyl group possibly being substituted with a dimethylamino group,
a group —(CH$_2$)$_p$-morpholinyl, —(CH$_2$)$_p$-pyrrolidinyl or —(CH$_2$)$_p$-tetrahydroisoquinoline, in which p may range from 0 to 4,
a group —(CH$_2$)$_p$-heteroaryl, in which p may range from 0 to 4 and in which the heteroaryl group is chosen from pyridyl, aminopyridyl, pyridyl N-oxide, pyrimidinyl, pyrazinyl, pyridazinyl, imidazolyl and pyrazolyl groups, the said heteroaryl group possibly being substituted, on a carbon atom and/or on a nitrogen atom, with one to three groups chosen from a (C1–C4)alkyl group or a phenyl group, this phenyl group itself possibly being substituted with one to three groups chosen from halogen atoms and (C1–C4)alkyl groups,
a heteroarylcarbonyl group, the heteroaryl group being chosen from furyl, pyridyl, pyrimidyl, pyrazinyl, pyridazinyl and imidazolyl groups,
a phenylcarbonyl group, the phenyl group possibly being substituted with a halogen atom,
a (C1–C6)alkylcarbonyl group,
a group —(CH$_2$)$_p$—COOR' in which p may range from 0 to 4 and in which R' represents a hydrogen atom or a (C1–C6)alkyl group, or alternatively
a phenylsulphonyl group optionally substituted on the phenyl nucleus with a halogen atom, a trifluoromethyl group, a (C1–C4)alkyl group, a nitro group or a (C1–C4)alkoxy group;

and when X represents a carbon atom:

R3 represents a hydrogen atom, a group —NR5R6, a group —NHCOR7, a group —CONHR5, a group —COR7, an —NHCONH$_2$ group, an —OH group or a —CH$_2$OH group, R4 represents:
a hydrogen atom,
a group —(CH$_2$)$_p$-phenyl, in which p may range from 0 to 4 and in which the phenyl nucleus is optionally substituted with one to three groups chosen, independently of each other, from: a (C1–C4)alkyl group, a nitro group, a hydroxyl group, an amino group, a halogen atom, a trifluoromethyl group, a (C1–C4)alkoxy group, a (C1–C4)alkylamino group, a (C1–C4)dialkylamino group, an —NHCHO group, a group —NHCOR or a group —NHSO$_2$R, in which R represents a (C1–C4)alkoxy group or a (C1–C4)alkyl group, this (C1–C4)alkyl group possibly being substituted with a dimethylamino group,
a group —(CH$_2$)$_p$-heteroaryl, in which p may range from 0 to 4 and in which the heteroaryl group is chosen from pyridyl, aminopyridyl, pyridyl N-oxide, pyrimidinyl, pyrazinyl, pyridazinyl, imidazolyl and pyrazolyl groups, the said heteroaryl group possibly being substituted, on a carbon atom and/or on a nitrogen atom, with one to three groups chosen from a (C1–C4)alkyl group or a phenyl group, this phenyl group itself possibly being substituted with one to three groups chosen from halogen atoms and (C1–C4)alkyl groups, or alternatively
a group —(CH$_2$)$_t$NR7R8, in which t is equal to 0 or 1,
R5 and R6 are as defined above,
R7 and R8 represent, independently of each other, a (C1–C4)alkyl or (C1–C4)alkoxy group, or together form a 5- to 7-membered saturated ring optionally comprising an additional nitrogen atom, this ring possibly being substituted with a (C1–C4)alkyl group on a carbon atom or a nitrogen atom, including on the nitrogen atom to which the groups R7 and R8 are attached, to form a quaternary ammonium, among which mention may be made of a 1-piperidyl group, a 1-pyrrolidinyl group or a 1-piperazinyl group.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of the invention may exist in the form of bases or addition salts with pharmaceutically acceptable acids. Such addition salts also form part of the invention.

In the context of the present invention, the following definitions apply:

a (Cq-Cr)alkyl group: a saturated, linear or branched aliphatic group containing from q to r carbon atoms, q and r being integers. Mention may be made especially of methyl, ethyl, propyl, isopropyl, n-propyl, butyl, isobutyl, tert-butyl, n-butyl, pentyl, etc. groups;

a halogen atom: a fluorine, chlorine, bromine or iodine atom, a (C3–C7)cycloalkyl group; a cyclic alkyl group containing from 3 to 7 carbon atoms. Mention may be made especially of cyclopropyl, cyclobutyl, cyclopentyl, cyclohexyl and cycloheptyl groups.

In the compounds of formula (I) which are the subjects of the invention, when X represents a carbon atom and when R4 represents a group —NR7R8, then R3 is preferably other than —NR5R6, —NHCOR7, —NHCONH$_2$ and —OH groups.

Among the compounds of formula (I) which are the subjects of the present invention, mention may be made of the preferred compounds for which:

R1, R2 and R9 represent, independently of each other, a hydrogen atom or a (C1–C4)alkyl group, R2' and R9' represent hydrogen atoms, X represents a nitrogen atom, m is equal to 1 or 2, R3 represents a (C1–C4)alkyl group to give compounds of formula (I) comprising a quaternary ammonium, or alternatively it does not exist, to give compounds of formula (I) comprising a secondary or tertiary amine, R4 represents a hydrogen atom, a (C1–C6)alkyl group, a (C3–C7)cycloalkyl group, a 4-piperidyl group, optionally substituted on a carbon atom or on the nitrogen atom with a (C1–C4)alkyl group, a group —(CH$_2$)$_p$—NR5R6, —(CH$_2$)$_p$—CONR5R6 or —CO—(CH$_2$)$_p$—NR5R6, in which p may range from 0 to 4 and in which R5 and R6 represent, independently of each other, a hydrogen atom or a (C1–C4)alkyl group, a group —(CH$_2$)$_p$-phenyl, in which p may range from 0 to 4 and in which the phenyl nucleus is optionally substituted with one to three groups chosen, independently of each other, from a nitro group, a halogen atom and a trifluoromethyl group, a group —(CH$_2$)$_p$-morpholinyl, —(CH$_2$)$_p$-pyrrolidinyl or —(CH$_2$)$_p$-tetrahydroisoquinoline, in which p may range from 0 to 4, a group —(CH$_2$)$_p$-pyrazolyl, in which p may range from 0 to 4 and in which the pyrazolyl group may be substituted, on a carbon atom and/or on a nitrogen atom, with one to three groups chosen from a (C1–C4)alkyl group or a phenyl group, a group —(CH$_2$)$_p$-pyridyl, in which p may range from 0 to 4, a heteroarylcarbonyl group, the heteroaryl group being chosen from a furyl group or a pyridyl group, a phenylcarbonyl group, the phenyl group possibly being substituted with a halogen atom, a (C1–C6)alkylcarbonyl group, a group —(CH$_2$)$_p$—COOR' in which p may range from 0 to 4 and in which R' represents a (C1–C6)alkyl group, or a phenylsulphonyl group;

Or alternatively the preferred compounds for which:

R1, R2' and R9' represent hydrogen atoms,

R2 and R9 represent, independently of each other, a hydrogen atom or a (C1–C4)alkyl group, X represents a carbon atom, m is equal to 1, R3 represents a hydrogen atom, a group —NR5R6, a group —NHCOR7, a group —CONHR5, a group —COR7, an —NHCONH$_2$ group, an —OH group or a —CH$_2$OH group, R4 represents a hydrogen atom, a phenyl group, a heteroaryl group chosen from an imidazolyl group, optionally substituted with a (C1–C4)alkyl group, a pyridyl group or a pyrazolyl group, optionally substituted on a nitrogen atom or on a carbon atom with a phenyl group which may itself be substituted with one to three groups chosen from halogen atoms and (C1–C4)alkyl groups, a group —NR7R8, R5 and R6 represent, independently of each other, a hydrogen atom or a (C1–C4)alkyl group, R7 and R8 represent, independently of each other, a (C1–C4)alkyl or (C1–C4)alkoxy group, or together form a saturated 5- to 7-membered ring optionally comprising an additional nitrogen atom, this ring possibly being substituted with a (C1–C4)alkyl group on a carbon atom or on a nitrogen atom, including on the nitrogen atom to which groups R7 and R8 are attached to form a quaternary ammonium, among which mention may be made of a 1-piperidyl group, a 1-pyrrolidinyl group or a 1-piperazinyl group.

Among the latter preferred compounds, the compounds that are most particularly preferred are those of formula (I) for which:

R1, R2 and R9 represent, independently of each other, a hydrogen atom or a (C1–C4)alkyl group, R2' and R9' represent hydrogen atoms, X represents a nitrogen atom, m is equal to 1 or 2, R3 represents a (C1–C4)alkyl group, to give compounds of formula (I) comprising a quaternary ammonium, or alternatively it does not exist, to give compounds of formula (I) comprising a secondary or tertiary amine, R4 represents a hydrogen atom, a (C1–C4)alkyl group, a (C3–C7)cycloalkyl group, a 4-piperidyl group optionally substituted on the nitrogen atom with a (C1–C4)alkyl group, a group —(CH$_2$)$_p$—NR5R6, —(CH$_2$)$_p$—CONR5R6 or —CO—(CH$_2$)$_p$—NR5R6, in which p is between 1 and 3 and in which R5 and R6 represent, independently of each other, (C1–C4)alkyl groups, a group —(CH$_2$)$_p$-phenyl, in which p may range from 0 to 4 and in which the phenyl nucleus is optionally substituted with one to three groups chosen, independently of each other, from a nitro group, a halogen atom (such as a chlorine or a fluorine) and a trifluoromethyl group, a group —(CH$_2$)$_p$-morpholinyl, —(CH$_2$)$_p$-pyrrolidinyl or —(CH$_2$)$_p$-tetrahydroisoquinoline, in which p is equal to 2 or 3, a group —(CH$_2$)$_p$-pyrazolyl, in which p may range from 0 to 4 and in which the pyrazole group may be substituted, on a carbon atom and/or on a nitrogen atom, with one to three groups chosen from a (C1–C4)alkyl group or a phenyl group, a group —(CH$_2$)$_p$-heteroaryl, in which p is equal to 0 or 1 and in which the heteroaryl group is a 4-pyridyl or 2-pyridyl group, a (C1–C4)alkylcarbonyl group, or a group —COOR' in which R' represents a (C1–C4)alkyl group;

Or alternatively the compounds that are most particularly preferred are those of formula (I) for which:

R1, R2' and R9' represent hydrogen atoms,

R2 and R9 represent, independently of each other, a hydrogen atom or a (C1–C4)alkyl group, X represents a carbon atom, m is equal to 1, R3 represents a hydrogen atom, an —NH2 group or a group —NHCOR7, R4 represents:

a phenyl group, a heteroaryl group chosen from an imidazolyl group optionally substituted with a (C1–C4)alkyl group, or a pyrazolyl group optionally substituted, on a carbon atom, with a phenyl group which may itself be substituted with one to three groups chosen from halogen atoms and (C1–C4) alkyl groups, or a group —NR7R8, in which R7 and R8 represent, independently of each other, a (C1–C4)alkyl or (C1–C4)alkoxy group, or together form a saturated 5- to 7-membered ring, this ring possibly being substituted with a (C1–C4)alkyl group on a carbon atom or on a nitrogen atom, including on the nitrogen atom to which the groups R7 and R8 are attached to form a quaternary ammonium, such as a 1-piperidyl group.

Other preferred compounds according to the invention may be defined as follows:

R1, R2, R2', R3, X and m are as defined above in relation to formula (I), R9 and R9' represent hydrogen atoms and when X represents a nitrogen atom, R4 represents:

a hydrogen atom, a (C1–C6)alkyl group, a (C3–C7)cycloalkyl group, a benzyl group optionally substituted on the phenyl nucleus with a halogen atom, a trifluoromethyl group, a (C1–C4)alkyl group, a nitro group or a (C1–C4)alkoxy group, a phenylethyl group, a heteroaryl group chosen from a pyridyl group, an aminopyridyl group, a pyrimidinyl group, a pyrazinyl group, a pyridazinyl group or an imidazolyl group, a heteroarylcarbonyl group, the heteroaryl group being chosen from a furyl group, a pyridyl group or a pyrimidyl, pyrazinyl, pyridazinyl or imidazolyl group, a phenylcarbonyl group, the phenyl group possibly being substituted with a halogen atom, a (C1–C6)alkylcarbonyl group, a group —(CH$_2$)$_p$—COOR in which p may range from 0 to 4 and in which R represents a (C1–C6)alkyl group, a phenylsulphonyl group optionally substituted on the phenyl nucleus with a halogen atom, a trifluoromethyl group, a (C1–C4)alkyl group, a nitro group or a (C1–C4) alkoxy group, or a phenyl group optionally substituted with one to three groups chosen, independently of each other, from: a (C1–C4)alkyl group, a nitro group, an amino group, a halogen atom, a trifluoromethyl group, a (C1–C4)alkoxy group, a (C1–C4)alkylamino group, a (C1–C4)dialkylamino group, an —NHCHO group or a group NHCOR, in which R represents a (C1–C4)alkoxy group or a (C1–C4)alkyl group, this (C1–C4)alkyl group possibly being substituted with a dimethylamino group, and when X represents a carbon atom, R4 represents:

a hydrogen atom, a phenyl group optionally substituted with one to three groups chosen, independently of each other, from: a (C1–C4)alkyl group, a nitro group, an amino group, a halogen atom, a trifluoromethyl group or a (C1–C4)alkoxy group, a heteroaryl group chosen from an imidazolyl group, optionally substituted with a (C1–C4)alkyl group, a pyridyl group, an aminopyridyl group, a pyrimidinyl group, pyrazinyl group or a pyridazinyl group, or a group —(CH$_2$)$_t$NR7R8, in which t is equal to 0 or 1, with the proviso that when R4 represents a group —NR7R8, R3 is other than —NR5R6, —NHCOR7, —HCONH$_2$ and —OH groups, R5 and R6 represent, independently of each other, a hydrogen atom or a (C1–C4)alkyl group, R7 and R8 represent, independently of each other, a (C1–C4)alkyl group or together form a saturated 5- to 7-membered ring optionally comprising an additional nitrogen atom, this ring possibly being substituted with a (C1–C4)alkyl group on a carbon atom or on a nitrogen atom, including on the nitrogen atom to which the groups R7 and R8 are attached to form a quaternary ammonium, among which mentioned may be made of a 1-piperidyl group, a 1-pyrrolidinyl group or a 1-piperazinyl group.

Other preferred compounds of formula (I) according to the invention may also be defined as follows: R1, R2, R2', R9, R9' and m are as defined above in relation to formula (I) and when X represents a nitrogen atom:

R3 is as defined above in relation to formula (I) according to the invention, and R4 represents:

a 4-piperidyl group substituted, on a carbon atom or on the nitrogen atom, with a (C1–C4)alkyl group, a group —(CH$_2$)$_p$—NR5R6 or —(CH$_2$)$_p$—CONR5R6, in which p may range from 1 to 4 and in which R5 and R6 represent, independently of each other, a (C1–C4)alkyl group, a group —CO—(CH$_2$)$_p$—NR5R6, in which p may range from 0 to 4 and in which R5 and R6 represent, independently of each other, a hydrogen atom or a (C1–C4)alkyl group;

a group —(CH$_2$)$_p$-phenyl, in which p may range from 1 to 4 and in which the phenyl nucleus is optionally substituted with one to three groups chosen, independently of each other, from: a (C1–C4)alkyl group, a nitro group, a hydroxyl group, an amino group, a halogen atom, a trifluoromethyl group, a (C1–C4)alkoxy group, a (C1–C4)alkylamino group, a (C1–C4)dialkylamino group, an —NHCHO group or a group —NHCOR, in which R represents a (C1–C4) alkoxy group or a (C1–C4)alkyl group, this (C1–C4)alkyl group possibly being substituted with a dimethylamino group, a group —(CH$_2$)$_p$-morpholinyl, —(CH$_2$)$_p$-pyrrolidinyl or —(CH$_2$)$_p$-tetrahydroisoquinoline, in which p may range from 1 to 4, a group —(CH$_2$)$_p$-heteroaryl, in which p may range from 1 to 4 and in which the heteroaryl group is chosen from pyridyl, aminopyridyl, pyrimidinyl, pyrazinyl, pyridazinyl, imidazolyl and pyrazolyl groups, the said heteroaryl group possibly being substituted, on a carbon atom and/or on a nitrogen atom, with one to three groups chosen from a (C1–C4)alkyl group or a phenyl group, a heteroarylcarbonyl group, the heteroaryl group being chosen from furyl, pyridyl, pyrimidyl, pyrazinyl, pyridazinyl and imidazolyl groups, a phenylcarbonyl group, the phenyl group possibly being substituted with a halogen atom, a (C1–C6)alkylcarbonyl group, a group —(CH$_2$)$_p$—COOR' in which p may range from 0 to 4 and in which R' represents a hydrogen atom or a (C1–C6)alkyl group, or a phenylsulphonyl group optionally substituted on the phenyl nucleus with a halogen atom, a trifluoromethyl group, a (C1–C4)alkyl group, a nitro group or a (C1–C4) alkoxy group;

and when X represents a carbon atom:

either R3 represents a group —NR5R6, in which R5 and R6 represent, independently of each other, a (C1–C4)alkyl group; a group —NHCOR7, in which R7 represents a (C1–C4)alkoxy group; a group —CONHR5, in which R5 represents a hydrogen atom or a (C1–C4)alkyl group; a group —COR7, in which R7 represents a (C1–C4)alkyl or (C1–C4)alkoxy group; or an —NHCONH$_2$ group, R4 being as defined above in relation to formula (I) according to the invention, or R3 is as defined above in relation to formula (I) according to the invention and R4 represents:

a phenyl group substituted with one to three groups chosen, independently of each other, from: a (C1–C4)alkyl group or a trifluoromethyl group, an imidazolyl group substituted with a (C1–C4)alkyl group, a pyrazolyl group substituted, on a nitrogen atom or on a carbon atom, with a phenyl group which may itself be substituted with one to three groups chosen from halogen atoms and (C1–C4)alkyl groups, a group —CH$_2$—NR7R8, in which R7 and R8 are as defined in claim 1, or a group —NR7R8, in which R7 and R8 represent, independently of each other, a (C1–C4)alkyl group or together form a saturated 5- to 7-membered ring optionally comprising an additional nitrogen atom, this ring possibly being substituted with a (C1–C4)alkyl group on a carbon atom or on a nitrogen atom, including on the nitrogen atom to which the groups R7 and R8 are attached to form a quaternary ammonium, among which mention may be made of a 1-piperidyl group, a 1-pyrrolidinyl group or a 1-piperazinyl group.

The preferred compounds in accordance with the invention, as defined above, may be in the form of enantiomers, diastereoisomers or mixtures of these various forms, including racemic mixtures, and also in the form of bases or addition salts with pharmaceutically acceptable acids.

In the text hereinbelow, the term "leaving group" means a group which may be readily cleaved from a molecule by breaking a heterolytic bond, with departure of an electron pair. This group may thus be readily replaced with another group, for example during a substitution reaction. Such leaving groups are, for example, halogens or an activated hydroxyl group such as a mesyl, tosyl, triflate, acetyl, etc. Examples of leaving groups and also references for preparing them are given in "Advances in Organic Chemistry", J. March, 3rd edition, Wiley Interscience, pp. 310–316.

To prepare the compounds of formula (I) in according to the invention, the process is performed according to synthetic scheme 1 below. According to this process, a derivative of formula (II), in which R1, R2, R2', R9 and R9' are as defined above and A represents a leaving group, preferably a halogen, is reacted in the presence of an amine of formula (III), in which X, R3, R4 and m are as defined above, in a solvent which may be an alcohol, such as isoamyl alcohol, an ether such as tetrahydrofuran or TGME (triethylene glycol monomethyl ether), dimethylformamide or a hydrocarbon such as toluene, at a temperature between room temperature and the boiling point of the solvent, to obtain the compound of formula (I). The reaction may be carried out in the presence of a base such as 2,6-lutidine or sodium tert-butoxide, in the presence of alkali metal halides such as potassium fluoride or in the presence of palladium-based or nickel-based catalysts, as described, for example, in patent application EP 646 583 or in *J. Med. Chem.* (1986) 29 1178–1183, *Tetrahedron Letters* (1997) 32 5607–5610, *Tetrahedron Letters* (1999) 55 12829–12842, *Tetrahedron Letters* (1999) 40 6875–6879.

When the compound of formula (I) comprises a free primary or secondary amine function, it may also be obtained by reacting a derivative of formula (II) with an amine of formula (III) in which the said amine function is protected by a conventional amine-protecting group such as a tert-butylcarbamate (BOC). The compound of formula (I) with a protected-amine function thus obtained is then treated according to one of the known methods to obtain the desired compound (I) containing a free amine function. Examples of amine-protecting groups and of deprotection methods are mentioned especially in T. W. Greene, P. G. M. Wuts, "Protective Groups in Organic Synthesis", J. Wiley, Ed., 1991.

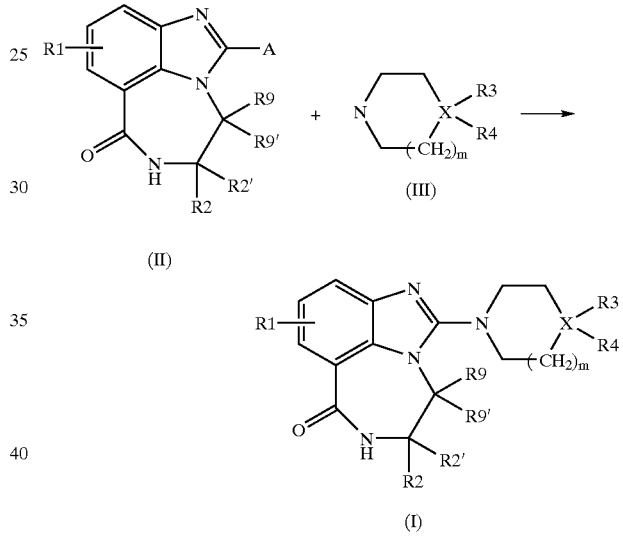

Synthetic scheme 1

The compounds of formula (II) may be prepared by a Schmidt reaction starting with compounds of formula (X) according to scheme 2, under the operating conditions that are known to those skilled in the art, in particular by reaction with sodium azide in chloroform in the presence of an acid such as sulphuric acid. The compounds of formula (X) may alternatively be prepared in one or two steps using a Beckmann reaction, either by reacting the oxine prepared from the ketone and hydroxylamine with, for example, phosphorus pentachloride, or by directly treating the ketone with hydroxylamine-O-sulphonic acid in the presence of formic acid.

The compounds of formula (X) may be prepared according to operating conditions that are known to those skilled in the art, in particular by reacting a compound of formula (IV), in which R1, R2, R2', R9 and R9' are as defined above, with a halogenating agent such as phosphoryl chloride.

The compounds of formula (IV) may be prepared according to a process described in synthetic scheme 2. According to one variant of this process, a diamine of formula (V), in which R1, R2, R2', R9 and R9' are as defined above, is condensed with a phosgene derivative such as carbonyldiimidazole (CDI). According to another variant, a derivative of formula (VI), in which R1 is as defined above, is alkylated with an agent of formula (VIII, R=(C1–C4)alkyl) in which R2, R9 and R9' are as defined above, to obtain the products of formula (VII) in which R2'=H or with an agent of formula (IX, R=(C1–C4)alkyl and Y is a leaving group), in which R2, R2', R9 and R9' are as defined above, to obtain the products of formula (VII). The compounds (VII) thus obtained are then converted into carboxylic acids (VII, R=H) or into acid derivatives such as acid chlorides (VII, R=Cl), and then cyclized according to operating conditions known to those skilled in the art to give the intermediates of formula (X) directly. A similar approach to this second variant is specially described in patent application JP 55 111 406 or in *Tetrahedron Letters* (1995), 36, 1387–1390.

Alternatively, the compounds of formula (X) in which R2 and R2' do not represent hydrogen atoms can be prepared from the corresponding compounds (X) in which R2' represents a hydrogen atom, by alkylation with a reagent of the type R2'Z in which Z represents a leaving group, preferably iodine. This reaction can be carried out in a solvent such as dimethylformamide, ether or tetrahydrofuran and in the presence of a base, according to the methods known to those skilled in the art.

The compounds of formulae (III), (V), (VI), (VIII) and (IX) are commercially available or may be prepared according to operating conditions that are known to those skilled in the art.

A subject of the present invention is also the synthetic intermediates of formula (II), which are novel.

The examples which follow illustrate the present invention. The numbers of the compounds illustrated refer to those in the table given later, which illustrates the chemical structures of a number of compounds according to the invention.

EXAMPLE 1

Preparation of Intermediates of Formula (II)

1.1. Preparation of 2-chloro-5,6dihydroimidazo[4,5,1-j,k][1,4]benzodiazepin-7-(4H)one
(A=Cl, R1=R2=R2'=R9=R9'=H)

1.1.1. 2-chloro-4,5-dihydroimidazo[4,5,1-i,j]quinolin-6-one

This compound is obtained from the compound 4H-imidazo[4,5,-i,j]-quinolin-2,6-(1H,5H)dione (IV), described in Japanese patent No. 55 111 406. 10 g of compound (IV) are reacted at reflux with 38.6 ml of phosphorus oxychloride and 6.3 g of ammonium chloride, for 1.5 hours in a 250 ml three-necked flask equipped with a condenser. The reaction mixture is then cooled and poured onto ice, to which is added 20% aqueous ammonia solution, with vigorous stirring, until a pH=9 is obtained. The mixture is extracted with twice 250 ml of ethyl acetate, dried over magnesium sulphate, filtered and evaporated. 9.81 g of a white solid are obtained, which is used without further purification in the next step. $^1$H NMR (200 MHz, δ ppm) DMSO-$d_6$: 7.8 (d, 1H), 7.5 (d, 1H), 7.3(t, 1H), 4.5(t, 2H), 3.0(t, 2H).

1.1.2. 2-chloro-5,6-dihydroimidazo[4,5,1-j,k][1,4]benzodiazepin-7-(4H)one

2-Chloro-4,5-dihydroimidazo[4,5,1-i,j]-quinolin-6-one (4 g, 19.35 mmol) dissolved in chloroform (48.5 ml, presence

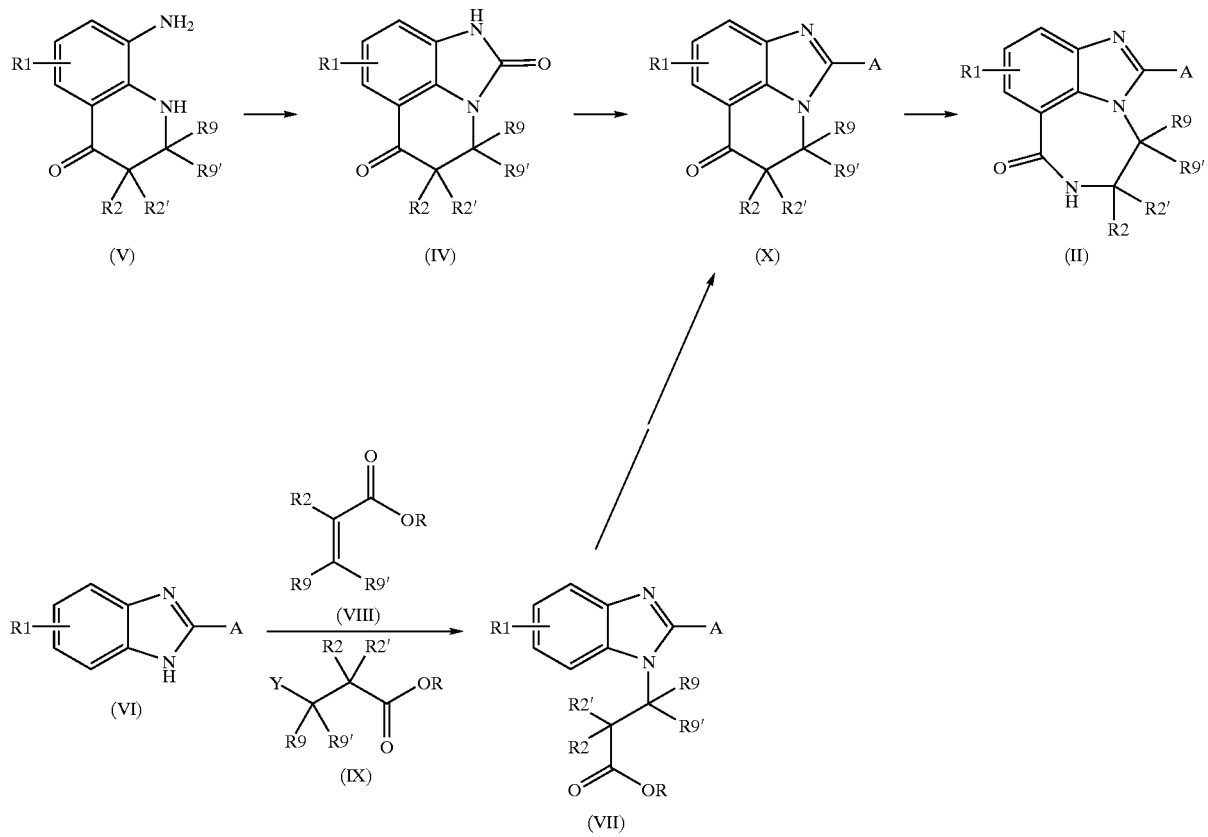

Synthetic scheme 2 of a small amount of insoluble material) is introduced into a 1 l three-necked flask under an argon atmosphere equipped with a magnetic stirrer, a contact thermometer and an addition funnel. The mixture is cooled to 0° C. (internal temperature) and sulphuric acid (20 ml) is first introduced dropwise over 10 minutes, followed by portionwise addition of sodium azide (4.72 g, 72.6 mmol) in solid form (the reaction is highly exothermic at the start), and the mixture is finally allowed to return to room temperature and is left stirring for 24 hours. The reaction mixture is hydrolysed with saturated sodium carbonate solution (~300 ml, pH>7) and extracted with chloroform (3×200 ml) and the organic phases are washed with water, combined and dried over magnesium sulphate. After filtration and concentration, the residue is chromatographed with a gradient of petroleum ether/ethyl acetate from 50/50 to 100% ethyl acetate, and then with a gradient of ethyl acetate/methanol from 95/5 to 80/20 to give the expected product (1.81 g, 42%) and the amide isomer (0.77 g, 18%). $^1$H NMR (200 MHz, δ ppm) DMSO-$d_6$: 3.63 (m, 2H), 4.32 (m, 2H), 7.38 (dd, 1H), 7.84 (d, 1H), 7.91 (d, 1H), 8.45 (m, 1H).

1.2. Preparation of 2-chloro-5,6-dihydro-5-methylimidazo[4,5,1-j,k][1,4]benzodiazepin-7-(4H)one
(A=Cl, R1=H, R2=CH$_3$, R2'=R9=R9'=H)

1.2.1. 2-chloro-5-methyl-4,5-dihydroimidazo[4,5,1-i,j]quinolin-6-one 1.2.1.1 Methyl 1-methyl-3-(2-chlorobenzimidazol-1-yl)propionate 2-Chloro-1H-benzimidazole (15.25 g, 100 mmol) dissolved in chloroform (100 ml) is introduced into a 1 l three-necked flask under a nitrogen atmosphere, equipped with a magnetic stirrer, an addition funnel an a condenser. Triton B (47 ml, 110 mmol) and methyl methacrylate (107 ml, 1 mol) are then added. The reaction is maintained at reflux for 2 hours and allowed to cool, and the chloroform is then evaporated off. The residue is taken up in ethyl acetate and the organic phase is washed 3 times with water and once with saturated sodium chloride solution. Flash chromatography of the crude product (16.0 g) on silica gel (1 kg) with an elution gradient of from 30 to 70% ethyl acetate in petroleum ether gives the expected product in the form of white crystals (10.1 g, 40%). $^1$H NMR (300 MHz, δ ppm) DMSO-$d_6$: 1.15 (d, 3H), 3.05 (m, 1H), 3.50 (s, 3H), 4.25 (dd, 1H), 4.50 (dd, 1H), 7.25 (m, 2H), 7.60 (m, 2H).

1.2.1.2 1-Methyl-3-(2-chlorobenzimidazol-1-yl)-propionic acid, lithium salt.

The ethyl ester from the preceding step (10.11 g, 40 mmol) dissolved in tetrahydrofuran (120 ml) is introduced into a 0.5 l one-necked round-bottomed flask equipped with a magnetic stirrer, followed by addition of aqueous lithium hydroxide solution (1.678 g, 40 mmol, 60 ml of distilled water). The mixture is left to react overnight at room temperature, the tetrahydrofuran and water are evaporated off and the residue is then taken up in methyl ether (2 l) and stirred for 2 hours. The white precipitate obtained is filtered off, washed with ethyl ether and then dried thoroughly under the vacuum of a vane pump over phosphorus pentoxide to give the expected product in the form of white crystals (9.48 g, 97%). The compound is used without further purification for the next step. $^1$H NMR (300 MHz, δ ppm) DMSO-$d_6$+ε D$_2$O: 1.35 (d, 3H), 2.60 (m, 1H), 4.10 (dd, 1H), 4.40 (dd, 1H), 7.25 (m, 2H), 7.55 (d, 1H), 7.60 (d, 1H) LC-MS: MH$^+$=239 (acid).

1.2.1.3 2-Chloro-5-methyl-4,5-dihydroimidazo[4,5,1-i,j]quinolin-6-one.

The lithium salt described above (4.74 g, 19.38 mmol) introduced into a 1 l three-necked flask under an argon atmosphere, equipped with a magnetic stirrer, a condenser and an addition funnel, followed by addition of 1,2-dichloroethane freshly distilled over phosphorus pentoxide (0.5 l). Oxalyl chloride (3.40 ml, 38.75 mmol) is added rapidly with stirring and the reaction mixture is heated at about 40° C. for 15 minutes. Aluminium chloride (7.75 g, 58 mmol) is added to the intermediate acid chloride thus obtained and the mixture is refluxed for 3 hours. The reaction mixture is allowed to cool and is then poured onto an ice/salt mixture and extracted with 1,2-dichloroethane, the organic phase is washed with saturated sodium chloride solution, dried over magnesium sulphate and filtered, and the solvent is then evaporated off. Flash chromatography of the crude product (4.84 g) on silica gel (420 g), eluting with a gradient of from 100% dichloromethane to a 90/10 dichloromethane/ethyl acetate mixture, gives the expected product in the form of white crystals (3.36 g, 78%). $^1$H NMR (300 MHz, δ ppm) DMSO-$d_6$: 1.40 (d, 3H), 3.20 (m, 1H), 4.10 (dd, 1H), 4.65 (dd, 1H), 7.45 (t, 1H), 7.70 (d, 1H), 7.85 (d, 1H). LC-MS: MH$^+$=221.

1.2.2. 2-Chloro-5,6-dihydro-5-methylimidazo[4,5,1-j,k][1,4]benzodiazepin-7-(4H)one.

The process is performed as in Example 1.1.2, by reacting 2.6 g of chloro derivative of formula (X), 30 ml of chloroform, 2.85 g of sodium azide and 12 ml of sulphuric acid. After chromatography twice on silica gel, the expected product (1.87 g, 68%) and traces of the amide isomer (0.08 g, 3%) are obtained. $^1$H NMR (300 MHz, δ ppm) CDCl$_3$: 1.45 (d, 3H), 4.00 (m, 1H), 4.11 (m, 1H), 4.42 (d, 1H), 7.37 (dd, 1H), 7.83 (d, 1H), 8.05 (d, 1H).

1.3. Preparation of 2-chloro-5,6-dihydro-10-methylimidazo[4,5,1-j,k][1,4]benzodiazepin-7-(4H)one
(A=Cl, R1=10-CH$_3$, R2=R'2=R9=R9'=H)

1.3.1. 2-Chloro-4,5-dihydro-9-methylimidazo[4,5,1-i,j]quinolin-6-one.

1.3.1.1. 2-Hydroxy-4-methylbenzimidazole.

2,3-Diaminotoluene (5 g, 41 mmol), 1,1-carbonyldiimidazole (7.3 g, 45 mmol) and 50 ml of anhydrous DMF are successively introduced into a 250 ml two-necked flask under an argon atomosphere, equipped with a magnetic stirrer. After heating the mixture at 90–95° C. for 4 hours, the solvent is distilled off under vacuum and the residue obtained is taken up in water (250 ml) and extracted with ethyl acetate (3×250 ml). The insoluble product formed during the extraction is recovered (4.8 g) and the combined organic phases are washed again with saturated NaCl solution, dried over MgSO$_4$, filtered and concentrated, allowing a further 1.2 g of desired product (6 g, quantitative) to be recovered. $^1$H NMR (300 MHz, δ ppm) DMSO-$d_6$: 2.27 (s, 3H), 6.72 (m, 2H), 6.82 (m, 1H).

1.3.1.2. 2-Chloro-4-methylbenzimidazole.

2-Hydroxy-4-methylbenzimidazole (5.92 g, 40 mmol) and 40 ml of phosphoryl chloride are introduced into a 250 ml two-necked flask under an argon atmosphere, equipped with a magnetic stirrer. The mixture is refluxed for 20 hours and the phosphoryl chloride is evaporated off under vacuum. The solid obtained is taken up in water (250 ml), the mixture is neutralized to pH=8 with 28% aqueous ammonia and the aqueous phase is extracted with ethyl acetate (3×250 ml). After the usual work-up, the 2-chloro-4-methylbenzimidazole is obtained in a yield of 93% (6.23 g). $^1$H NMR (300 MHz, δ ppm) DMSO-$d_6$: 2.47 (s, 3H), 7.01 (d, 1H), 7.11 (t, 1H), 7.32 (d, 1H).

1.3.1.3. Methyl 1-methyl-3-(2-chloro-4-methylbenzimidazol-1-yl)propionate.

This compound is prepared according to the procedure described in Example 1.2.1.1. (7.85 g, 94%). $^1$H NMR (300

MHz, δ ppm) DMSO-d$_6$: 2.48 (s, 3H), 2.86 (t, 2H), 3.56 (s, 3H), 4.49 (t, 2H), 7.06 (d, 1H), 7.19 (t, 1H), 7.44 (d, 1H).

1.3.1.4. 1-Methyl-3-(2-chloro-4-methylbenzimidazol-1-yl) propionic acid, sodium salt.

This compound is prepared according to the procedure described in Example 1.2.1.2 (6.94 g, 94%). $^1$H NMR (300 MHz, δ ppm) DMSO-d$_6$: 2.3 (dd, 2H), 2.48 (s, 3H), 4.32 (dd, 2H), 7.01 (d, 1H), 7.15 (t, 1H), 7.41 (d, 1H) (acid).

1.3.1.5. 2-Chloro-4,5-dihydro-9-methylimidazo[4,5,1-i,j] quinolin-6-one.

This compound is prepared according to the procedure described in Example 1.2.1.3 (4.72 g, 76%). $^1$H NMR (300 MHz, δ ppm) DMSO-d$_6$ 2.58 (s, 3H), 3.05 (t, 2H), 4.53 (t, 2H), 7.19, d, 1H), 7.52 (d, 1H).

1.3.2. 2-Chloro-5,6-dihydro-10-methyl-imidazo[4,5,1-j, k][1,4]benzodiazepin-7-(4H)one.

The process is performed as in Example 1.1.2, by reacting 1.9 g of chloro derivative described in Example 1.3.1.5, 25 ml of chloroform, 2.10 g of sodium azide and 9 ml of sulphuric acid. After chromatography twice on silica gel (95/5/0.5 dichloromethane/methanol/aqueous ammonia followed by a gradient of 90/10 methanol/aqueous ammonia of from 0% to 7% in dichloromethane) the expected product (0.78 g, 38.4%) and a mixture of the expected compound and of the amide isomer (0.77 g, 38%) are obtained. $^1$H NMR (300 MHz, δ ppm) DMSO-d$_6$: 2.56 (s, 3H), 3.61 (m, 2H), 4.32 (broad s, 2H), 7.19 (d, 2H), 7.79 (d, 2H), 8.35 (t, NH amide).

EXAMPLE 2

2-(4-phenyl-piperazin-1-yl)-5,6-dihydroimidazo[4,5, 1-j,k][1,4]benzodiazepin-7-(4H)one (compound 1)

(R1=R2=R2'=R9=R9'=H, R3=—, X=N, R4=phenyl, m=1).

The intermediate of formula (II) from point 1.1 (0.2 g, 0.903 mmol), 1 ml of triethylene glycol monomethyl ether (TGME), 2,6-lutidine (0.116 ml, 0.993 mmol), cesium fluoride (0.137 g, 0.903 mmol) and 1-phenylpiperazine (0.152 ml, 0.993 mmol) dissolved in TGME (1 ml) are successively introduced into a round-bottomed flask equipped with a condenser and a magnetic stirrer. The reaction mixture is heated at 140° C. for 3 hours, allowed to cool and extracted twice with ethyl acetate. The organic phases are washed twice with water, dried over sodium sulphate, filtered and concentrated. The residue obtained is chromatographed on silica gel (98/2 dichloromethane/methanol) to give the expected compound (0.167 g, 53%), LC-MS: MH+=348. $^1$H NMR (360 MHz, δ ppm) DMSO-d$_6$: 3.32 (m, 4H), 3.45 (m, 4H), 3.51 (m, 2H), 4.21 (m, 2H), 6.82 (t, 1H), 7.02 (d, 2H), 7.20 (dd, 1H), 7.25 (m, 2H), 7.62 (d, 2H), 8.38 (m, 1H).

EXAMPLE 3

2-[4-(4-pyridyl)piperazin-1-yl]-5,6-dihydroimidazo [4,5,1-j,k][1,4]benzodiazepin-7-(4H)one (compound 2)

(R1=R2=R2'=R9=R9'=H, R3=—, X=N, R4=4-pyridyl, m=1)

The intermediate of formula (II) described in point 1.1 (0.2 g, 0.907 mmol), TGME (1 ml), 2,6-lutidine (0.117 ml, 0.998 mmol), cesium fluoride (0.138 g, 0.907 mmol) and 1-(4-pyridyl)piperazine (0.163 g, 0.998 mmol) dissolved in 1 ml of TGME are successively introduced into a round-bottomed flask equipped with a condenser and a magnetic stirrer. The reaction mixture is heated at 120° C. for 3 hours and allowed to cool, saturated sodium carbonate solution is added and the resulting mixture is extracted 4 times with dichloromethane. The organic phases are washed twice with saturated sodium chloride solution, dried over sodium sulphate, filtered and concentrated. The residue obtained is chromatographed on silica gel (95/5/0.1 dichloromethane/ methanol/NH4OH) to give the expected compound in the form of an off-white solid (0.128 g, 41%). LC-MS: MH+= 348. $^1$H NMR (500 MHz, δ ppm) DMSO-d$_6$: 3.40 (m, 4H), 3.49 (m, 6H), 4.21 (t, 2H), 6.89 (d, 2H), 7.18 (dd, 1H), 761 (m, 2H), 8.2 (d, 2H), 8.35 (t, 1H).

EXAMPLE 4

2-[4-(1-piperidyl)piperid-1-yl]-5,6-dihydroimidazo [4,5,1-j,k][1,4]benzodiazepin-7-(4H)one (compound 3)

(R1=R2=R2'=R9=R9'=R3=H, X=C, R4=1-piperidyl, m=1)

The intermediate of formula (II) described in point 1.1 (0.2 g, 0.907 mmol), TGME (1 ml), 2,6-lutidine (0.125 ml, 1.066 mmol), cesium fluoride (0.148 g, 0.969 mmol) and 4-piperidinopiperidine (0.180 g, 1.066 mmol) dissolved in 1 ml of TGME are successively introduced into a round-bottomed flask equipped with a condenser and a magnetic stirrer. The reaction mixture is heated at 140° C. for 4 hours and allowed to cool, saturated sodium carbonate solution is added and the resulting mixture is extracted twice with ethyl acetate and 4 times with dichloromethane. The organic phases are washed with water, dried over sodium sulphate, filtered and concentrated. The residue is chromatographed on silica gel (85/15/0.1 dichloromethane/methanol/NH$_4$OH) and the compound obtained is crystallized from a chloroform/ether mixture to give the title compound in the form of a white solid (0.155 g, 49%). LC-MS: MH+=353. $^1$H NMR (500 MHz, δ ppm) DMSO-d$_6$: 1.38 (m, 2H), 1,48 (m, 4H), 1.65 (m, 2H), 1.79 (m, 2H), 2.49 (m, 1H), 2.88 (m, 2H), 3.28 (m, 4H), 3.47 (t, 2H), 3.64 (m, 2H), 4.12 (m, 2H), 7.15 (dd, 1H), 7.56 (m, 2H), 8.31 (t, 1H).

EXAMPLE 5

2-[4-(5-methyl-1H-imidazo-4-yl)piperid-1-yl]-5,6-dihydroimidazo[4,5,1-j,k]-[1,4]benzodiazepin-7-(4H)one (compound 4)

(R1=R2=R2'=R3=R9=R9'=H, X=C, R4=5-methyl-1H-imidazol-4-yl, m=1)

The intermediate of formula (II) described in point 1.1 (0.2 g, 0.907 mmol), DMF (1.5 ml), 2,6-lutidine (0.117 ml, 0.998 mmol), cesium fluoride (0.138 g, 0.907 mmol) and 4-(5-methyl-1H-imidazo-4-yl)piperidine (0.375 g, 2.27 mmol) dissolved in 1 ml of DMF are successively introduced into a round-bottomed flask equipped with a condenser and a magnetic stirrer. The reaction mixture is heated at 140° C. for 2 hours and allowed to cool, saturated sodium bicarbonate solution and saturated sodium chloride solution are added and the resulting mixture is extracted 4 times with dichloromethane. The organic phases are washed twice with saturated sodium chloride solution, dried over sodium sulphate, filtered and concentrated. The residue is chromatographed on silica gel (90/10/0.1 dichloromethane/methanol/ NH$_4$OH) and the compound obtained is crystallized from a methanol (minimum)/dichloromethane/ether mixture to give the expected compound in the form of a white solid (0.175 g, 55%). LC-MS: MH+=350. $^1$H NMR (500 MHz, δ ppm) DMSO-d$_6$: 1.71 (m, 2H), 1.94 (m, 2H), 2.14 (m, 3H), 2.79 (m, 1H), 3.01 (m, 2H), 3.50 (m, 2H), 3.69 (m, 2H), 4.15 (m, 2H), 7.16 (dd, 1H), 7,34 (s, 1H), 7.58 (d, 2H), 8.33 (m, 1H), 11.54 (m, 1H).

EXAMPLE 6

2-(4-phenylpiperazin-1-yl)-5,6-dihydro-5-methylimidazo[4,5,1-j,k][1,4]benzodiazepin-7-(4H)one (compound 5)

(R1=R2'=R9=R9'=H, R3=—, R2=methyl, X=N, R4=phenyl, m=1)

The intermediate of formula (II) from point 1.2 (0.2 g, 0.849 mmol), TGME (1 ml), 2,6-lutidine (0.109 ml, 0.934 mmol), cesium fluoride (0.129 g, 0.849 mmol) and 1-phenylpiperazine (0.152 g, 0.934 mmol) dissolved in TGME (1 ml) are successively introduced into a round-bottomed flask equipped with a condenser and a magnetic stirrer. The reaction mixture is heated at 140° C. for 3 hours, allowed to cool and extracted twice with ethyl acetate. The organic phases are washed twice with water, dried over sodium sulphate, filtered and concentrated. The residue obtained is chromatographed on silica gel with ethyl acetate as eluent. The expected compound is obtained by crystallization from a dichloromethane/ethyl acetate mixture (0.2 g, 65%). LC-MS: MH+=362.

$^1$H NMR (500 MHz, δ ppm) DMSO-$d_6$: 1.27 (d, 3H), 3.27 (m, 2H), 3.36 (m, 4H), 3.50 (m, 2H), 3.79 (m, 1H), 4.10 (m, 2H), 6.81 (t, 1H), 7.00 (d, 2H), 7.18 (dd, 1H), 7.24 (t, 2H), 7.60 (d, 2H), 8.18 (d, 1H).

EXAMPLE 7

2-(4-N-tert-butyloxycarbonyl-piperazin-1-yl)-5,6-dihydroimidazo[4,5,1-j,k]-[1,4]benzodiazepin-7-(4H)one (compound 15)

(R1=R2=R2'=R9=R9'=H, R3=—, X=N, R4=tert-butyloxycarbonyl, m=1)

The chloro intermediate described in point 1.1.2. (0.4 g, 1.9 mmol), TGME (4 ml), lutidine (0.245 ml, 2.09 mmol), cesium fluoride (0.29 g, 1.9 mmol) and 4-N-tert-butyloxycarbonylpiperazine (0.369 g, 2.09 mmol) are successively introduced into a round-bottomed flask equipped with a condenser and a magnetic stirrer. The reaction mixture is heated at 140° C. for 6 hours and allowed to cool, water is added and the resulting mixture is extracted twice with dichloromethane. The organic phases are washed twice with water, dried over sodium sulphate, filtered and concentrated. Chromatography of the residue on silica gel (gradient of from 0% to 10% methanol in dichloromethane) gives the title product (0.369 g, 56%). $^1$H NMR (500 MHz, δ ppm) DMSO-$d_6$: 1.42 (s, 9H), 3.22 (m, 4H), 3.49 (m, 4H), 4.14 (m, 2H), 7.17 (t, 1H), 7.60 (m, 2H), 8.34 (m, 1H).

EXAMPLE 8

2-(4-piperazin-1-yl)-5,6-dihydroimidazo[4,5,1-j,k][1,4]benzodiazepin-7-(4H)one dihydrochloride (compound 16)

(R1=R2=R2'=R4=R9=R9'=H, R3=—, X=N, m=1)

A solution of hydrogen chloride (gas) in ether (10 ml) is added to a solution of the compound of Example 7 (0.205 g, 0.55 mmol) in methanol (20 ml) and the mixture is stirred magnetically at room temperature for 5 hours. The reaction mixture is concentrated and the expected compound is obtained after crystallization from methanol (0.182 g, 96%).
$^1$H NMR (500 MHz, δ ppm) DMSO-$d_6$: 3.29 (m, 2H), 3.52 (m, 4H), 3.69 (m, 4H), 4.20 (m, 2H), 7.35 (dd, 1H), 7.72 (m, 2H), 8.54 (m, 1H), 9.44 (m, 2H).

EXAMPLE 9

2-(4-N-tert-butyloxycarbonyl-piperazin-1-yl)-5-methyl-5,6-dihydroimidazo[4,5,1-j,k]-[1,4]benzodiazepin-7-(4H)one (compound 7)

(R2=CH$_3$, R1=R2'=R9=R9'=H, R3=—, X=N, R4=tert-butyloxycarbonyl, m=1)

The process is performed as indicated in Example 7, using the chloro intermediate described in point 1.2.2, to give the title compound in a yield of 80% (1.07 g). $^1$H NMR (360 MHz, δ ppm) DMSO-$d_6$: 1.26 (m, 3H), 1.43 (s, 9H), 3.17 (m, 2H), 3.45 (m, 2H), 3.55 (m, 2H), 3.78 (m, 2H), 4.05 (m, 2H), 7.18 (t, 1H), 7.60 (d, 2H), 8.22 (m, 1H).

EXAMPLE 10

2-(4-piperazin-1-yl)-5-methyl-5,6-dihydroimidazo[4,5,1-j,k][1,4]benzodiazepin-7-(4H)one dihydrochloride (compound 9)

(R2=CH$_3$, R1=R2'=R4=R9=R9'=H, R3=—, X=N, m=1)

The process is performed as indicated in Example 8, to give the title compound in quantitative yield (0.36 g). $^1$H NMR (360 MHz, δ ppm) DMSO-$d_6$: 1.29 (m, 3H), 3.25 (m, 2H), 3.37 (m, 2H), 3.67 (m, 2H), 3.80 (m, 4H), 4.12 (m, 2H), 7.39 (t, 1H), 7.72 (m, 2H), 8.43 (m, 1H), 9.53 (m, 2H).

EXAMPLE 11

2-(4-phenyl-4-tert-butyloxycarbonylaminopiperid-1-yl)-5,6-dihydroimidazo[4,5,1-j,k][1,4]benzodiazepin-7-(4H)one (compound 17)

(R1=R2=R2'=R9=R9'=H, R4=phenyl, X=C, R3=—NH-tert-butyloxycarbonyl, m=1)

The process is performed as in Example 7, by reacting 0.5 g (2.26 mmol) of chloro derivative of Example 1.1.2, 0.345 g (2.26 mmol) of cesium fluoride, 0.29 ml (2.49 mmol) of lutidine and 0.69 g (2.49 mmol) of 4-phenyl-4-tert-butyloxycarbonylaminopiperidine in 2 ml of TGME at 140° C. for 3.5 hours. After the usual work-up, purification by chromatography on silica gel (gradient of methanol in dichloromethane of from 0 to 12%) and crystallization (dichloromethane with a small amount of methanol/ether), the title compound is obtained in a yield of 70% (0.73 g). $^1$H NMR (500 MHz, δ ppm) DMSO-$d_6$: 1.35 (s, 9H), 2.05 (m, 2H), 2.40 (m, 2H), 3.23 (m, 2H), 3.47 (m, 4H), 4.17 (m, 2H), 7.16 (dd, 1H), 7.21 (m, 1H), 7.33 (m, 2H), 7.39 (m, 2H), 7,58 (m, 2H), 8.32 (m, 1H).

EXAMPLE 12

2-(4-phenyl-4-aminopiperid-1-yl)-5,6-dihydroimidazo[4,5,1-j,k][1,4]benzodiazepin-7-(4H)one dihydrochloride (compound 20)

(R1=R2=R2'=R9=R9'=H, R4=phenyl, X=C, R3=NH2, m=1)

The process is performed as indicated in Example 8 to give the title compound in a yield of 80% (0.403 g). $^1$H NMR (360 MHz, δ ppm) DMSO-$d_6$: 2.37 (m, 2H), 2.57 (m, 2H), 3.92 (m, 2H), 4.20 (m, 2H), 7.39 (t, 1H), 7.44 (m, 1H), 7.51 (m, 2H), 7.70 (m, 3H), 7.74 (d, 1H), 8.60 (m, 1H), 8.81 (m, 4H).

EXAMPLE 13

2-(4-cyclohexylpiperazin-1-yl)-5,6-dihydro-10-methylimidazo[4,5,1-j,k][1,4]benzodiazepin-7-(4H)one (compound 33)
($R1=10\text{-}CH_3$, $R2=R2'=R9=R9'=H$, $R3=-$, $X=N$, $R4=$cyclohexyl, m=1)

The chloro intermediate described in point 1.3.2 (0.2 g, 0.85 mmol), TGME (2 ml), lutidine (0.109 ml, 0.935 mmol), cesium fluoride (0.129 g, 0.85 mmol) and 4-N-cyclohexylpiperazine (0.158 g, 0.935 mmol) are successively introduced into a round-bottomed flask equipped with a condenser and a magnetic stirrer. The reaction mixture is heated at 140° C. for 8 hours. After the usual work-up, purification by chromatography on silica gel (gradient of methanol in dichloromethane of from 0 to 13%) and crystallization (dichloromethane/ether with a small amount of pentane), the title compound is obtained in a yield of 30% (0.092 g). $^1$H NMR (500 MHz, δ ppm) DMSO-$d_6$: 1.09 (m, 1H), 1.22 (m, 4H), 1.58 (m, 1H), 1.76 (m, 4H), 2.29 (m, 1H), 2.48 (s, 3H), 2.64 (m, 4H), 3.22 (m, 4H), 3.45 (m, 2H), 4.10 (m, 2H), 6.98 (d, 1H), 7.49 (d, 1H), 8.22 (m, 1H).

In the table which follows:

- in the "salt" column, "HCl" corresponds to a hydrochloride and the ratio in parentheses is the (acid:base) ratio,
- "Pr" represents a propyl group,
- the NMR analyses correspond to proton NMRs. Except where otherwise mentioned, the measurements are carried out in DMSO-$d_6$. * and ** mean that the measurements are carried out, respectively, at 360 MHz and at 500 MHz. If no indication of this type is given, then the measurement is carried out at 200 MHz.

TABLE

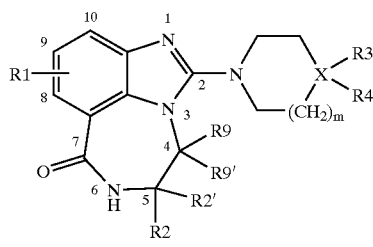

(I) in which $R2' = R9' = H$

| No. | R1 | R2 | R9 | R3 | R4 | X | m | Salt | NMR |
|---|---|---|---|---|---|---|---|---|---|
| 1 | H | H | H | — | phenyl | N | 1 | — | 3.32(m, 4H), 3.45(m, 4H), 3.51(m, 2H), 4.21(m, 2H) 6.82(t, 1H), 7.02(d, 2H), 7.20(dd, 1H), 7.25(m, 2H), 7.62(d, 2H), 8.38(m, 1H)** |
| 2 | H | H | H | — | 4-pyridyl | N | 1 | — | 3.40(m, 4H), 3.49(m, 6H), 4.21(t, 2H), 6.89(d, 2H) 7.18(dd, 1H), 761(m, 2H), 8.2(d, 2H), 8.35(t, 1H)** |
| 3 | H | H | H | H | piperidinyl | C | 1 | — | 1.38(m, 2H), 1.48(m, 4H), 1.65(m, 2H), 1.79(m, 2H), 2.49(m, 1H), 2.88(m, 2H), 3.28(m, 4H), 3.47(t, 2H), 3.64(m, 2H), 4.12(m, 2H), 7.15(dd, 1H), 7.56(m, 2H), 8.31(t, 1H)** |
| 4 | H | H | H | H | 4-methylimidazolyl | C | 1 | — | 1.71(m, 2H), 1.94(m, 2H), 2.14(m, 3H), 2.79(m, 1H), 3.01(m, 2H), 3.50(m, 2H), 3.69(m, 2H), 4.15(m, 2H), 7.16(dd, 1H), 7.34(s, 1H), 7.58(d, 2H), 8.33(m, 1H), 11.54(m, 1H)** |
| 5 | H | —CH$_3$ | H | — | phenyl | N | 1 | — | 1.27(d, 3H), 3.27(m, 2H), 3.36(m, 4H), 3.50(m, 2H), 3.79(m, 1H), 4.10(m, 2H), 6.81(t, 1H), 7.00(d, 2H), 7.18(dd, 1H), 7.24(t, 2H), 7.60(d, 2H), 8.18(d 1H)** |
| 6 | H | H | H | — | —CH$_3$ | N | 1 | — | 2.24(1, 3H), 3.28(m, 4H), 3.49(m, 2H), 4.12(m, 2H), 7.17(t, 1H), 7.59(d, 2H), 8.36(m, 1H)* |
| 7 | H | —CH$_3$ | H | — | —COOC(CH$_3$)$_3$ | N | 1 | — | 1.26(m, 3H), 1.43(s, 9H), 3.17(m, 2H), 3.45(m, 2H), 3.55(m, 2H), 3.78(m, 2H), 4.05(m, 2H), 7.18(t, 1H), 7.60(d, 2H), 8.22(m, 1H)* |

TABLE-continued

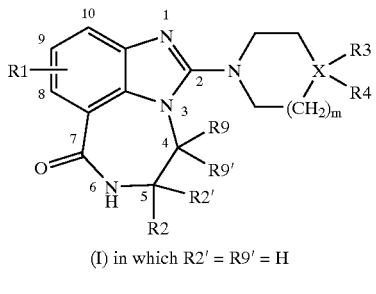

(I) in which R2' = R9' = H

| No. | R1 | R2 | R9 | R3 | R4 | X | m | Salt | NMR |
|---|---|---|---|---|---|---|---|---|---|
| 8 | H | H | H | — | 2-pyridyl | N | 1 | — | 3.32(m, 4H), 3.52(m, 2H), 3.68(m, 4H), 4.22(m, 2H), 6.69(t, 1H), 6.91(d, 1H), 7.19(t, 1H), 7.59(m, 3H), 8.15(m, 1H), 8.38(m, 1H)* |
| 9 | H | —CH$_3$ | H | — | H | N | 1 | HCl (2:1) | 1.29(m, 3H), 3.25(m, 2H), 3.37(m, 2H), 3.67(m, 2H), 3.80(m, 4H), 4.12(m, 2H), 7.39(t, 1H), 7.72(m, 2H), 8.43(m, 1H), 9.53(m, 2H)* |
| 10 | H | —CH$_3$ | H | — | —COCH$_3$ | N | 1 | — | 1.27(m, 3H), 2.06(s, 3H), 3.23(m, 2H), 3.36(m, 2H), 3.57(m, 2H), 3.66(m, 2H), 3.79(m, 4H), 4.07(m, 2H), 7.19(t, 1H), 7.60(d, 2H), 8.22(m, 1H)* |
| 11 | H | H | H | — | 4-nitrophenyl | N | 1 | — | 3.44(m, 4H), 3.52(m, 2H), 3.66(m, 4H), 4.23(m, 2H), 7.12(d, 2H), 7.20(t, 1H), 7.62(d, 2H), 8.10(d, 2H), 8.38(m, 1H)* |
| 12 | H | H | H | — | 4-fluorophenyl | N | 1 | — | 3.28(m, 4H), 3.42(m, 4H), 3.51(m, 2H), 4.20(m, 2H), 7.06(m, 4H), 7.19(t, 1H), 7.62(d, 2H), 8.37(m, 1H)* |
| 13 | H | H | H | — | 2-chlorophenyl | N | 1 | — | 3.18(m, 4H), 3.46(m, 4H), 3.52(m, 2H), 4.16(m, 2H), 7.08(m, 1H), 7.20(m, 2H), 7.34(m, 1H), 7.45(d, 1H), 7.62(d, 2H), 8.37(m, 1H)* |
| 14 | H | H | H | — | —CH$_3$ | N | 2 | — | 1.91(dd, 2H), 2.28(s, 3H), 2.58(m, 2H), 2.69(m, 2H), 3.46(m, 2H), 3.55(m, 4H), 4.12(m, 2H), 7.11(dd, 1H), 7.48(m, 2H), 8.30(m, 1H)** |
| 15 | H | H | H | — | —COOC(CH$_3$)$_3$ | N | 1 | — | 1.42(s, 9H), 3.22(m, 4H), 3.49(m, 4H), 4.14(m, 2H), 7.17(t, 1H), 7.60(m, 2H), 8.34(m, 1H)** |
| 16 | H | H | H | — | H | N | 1 | HCl (2:1) | 3.29(m, 2H), 3.52(m, 4H), 3.69(m, 4H), 4.20(m, 2H), 7.35(dd, 1H), 7.72(m, 2H), 8.54(m, 1H), 9.44(m, 2H)** |
| 17 | H | H | H | —NHCOOC(CH$_3$)$_3$ | phenyl | C | 1 | — | 1.35(s, 9H), 2.05(m, 2H), 2.40(m, 2H), 3.23(m, 2H), 3.47(m, 4H), 4.17(m, 2H), 7.16(dd, 1H), 7.21(m, 1H), 7.33(m, 2H), 7.39(m, 2H), 7.58(m, 2H), 8.32(m, 1H)** |
| 18 | H | H | H | — | —CH$_2$CH$_2$-morpholinyl | N | 1 | — | 2.38(m, 4H), 2.43(m, 2H), 2.58(m, 2H), 3.24(m, 4H), 3.47(m, 2H), 3.55(m, 4H), 4.12(m, 2H), 7.16(t, 1H), 7.58(m, 2H), 8.33(m, 1H)** |
| 19 | H | H | H | — | N-methylpiperidin-4-yl | N | 1 | — | 1.43(m, 2H), 1.72(m, 2H), 1.83(m, 2H), 2.12(s, 3H), 2.19(m, 1H), 2.64(m, 4H), 2.78(m, 2H), 3.24(m, 4H), 3.47(m, 2H), 4.12(m, 2H), 7.15(t, 1H), 7.57(m, 2H), 8.32(m, 1H)** |

TABLE-continued (I) in which R2′ = R9′ = H

| No. | R1 | R2 | R9 | R3 | R4 | X | m | Salt | NMR |
|---|---|---|---|---|---|---|---|---|---|
| 20 | H | H | H | —NH₂ | (phenyl) | C | 1 | HCl (2:1) | 2.37(m, 2H), 2.57(m, 2H), 3.92(m, 2H), 4.20(m, 2H), 7.39(t, 1H), 7.44(m, 1H), 7.51(m, 2H), 7.70(m, 3H), 7.74(d, 1H), 8.60(m, 1H), 8.81(m, 4H)** |
| 21 | H | H | H | — | —CH₂—CON(CH₂—CH₃)₂ | N | 1 | — | 1.013(t, 3H), 1.40(t, 3H), 2.62(m, 4H), 3.20(s, 2H), 3.24(m, 6H), 3.30(s, 1H), 3.38(q, 2H), 3.48(m, 2H), 4.12(m, 2H), 7.16(t, 1H), 7.58(m, 2H), 8.33(t, 1H)** |
| 22 | H | H | H | — | (butyl-pyrrolidine) | N | 2 | — | 1.55(m, 2H), 1.63(m, 4H), 1.90(m, 2H), 2.35(m, 6H), 2.46(t, 2H), 2.65(m, 2H), 2.77(m, 2H), 3.46(m, 2H), 3.54(m, 4H), 4.12(m, 2H), 7.11(t, 1H), 7.47(m, 2H), 8.30(t, 1H)** |
| 23 | H | —CH₃ | H | — | —(CH₂)₃—N(CH₃)₂ | N | 1 | — | 1.25(m, 3H), 1.59(m, 2H), 2.15(s, 6H), 2.27(m, 2H), 2.35(m, 2H), 2.57(m, 2H), 3.16(m, 2H), 3.77(m, 1H), 4.01(m, 2H), 7.16(t, 1H), 7.57(d, 2H), 8.17(m, 1H)** |
| 24 | H | H | H | — | (ethyl-pyridine) | N | 1 | — | 2.57(m, 4H), 3.30(m, 2H), 3.47(s, 2H), 4.11(m, 2H), 7.16(t, 1H), 7.36(d, 2H), 7.58(d, 2H), 8.33(t, 1H), 8.52(d, 2H)** |
| 25 | H | H | H | — | (4-CF₃-phenyl) | N | 1 | — | 3.46(m, 10H), 4.22(m, 2H), 7.15(d, 2H), 7.19(t, 1H), 7.55(d, 2H), 7.62(d, 2H), 8.39(t, 1H)* |
| 26 | H | H | H | — | (butyl-phenyl) | N | 1 | — | 1.76(q, 2H), 2.35(t, 2H), 2.51(m, 4H), 2.61(t, 2H), 3.27(m, 4H), 3.47(m, 2H), 4.12(m, 2H), 7.16(t, 2H), 7.22(m, 2H), 7.27(m, 2H), 7.58(m, 2H), 8.33(t, 1H)** |
| 27 | H | H | H | H | (2-F-methyl-phenyl) | N | 1 | — | 3.23(m, 4H), 3.45(m, 4H), 3.51(m, 2H), 4.2(t, 2H), 7.01(m, 1H), 7.13(m, 3H), 7.19(t, 1H), 7.62(dd, 2H), 8.38(t, 1H)* |
| 28 | H | H | H | — | (dimethyl-ethyl-phenyl-pyrazole) | N | 1 | — | 2.20(s, 3H), 2.28(s, 3H), 2.56(m, 3H), 3.26(m, 4H), 3.78(s, 2H), 3.68(m, 2H), 4.13(m, 2H), 7.16(t, 1H), 7.37(m, 1H), 7.48(m, 4H), 7.58(d, 2H), 8.23(m, 1H)** |
| 29 | H | H | H | H | (methyl-(4-F-phenyl)-pyrazole) | C | 1 | — | 1.87(m, 2H), 2.05(m, 2H), 2.92(m, 1H), 3.07(m, 2H), 3.50(m, 2H), 3.70(m, 2H), 4.17(m, 2H), 7.17(t, 1H), 7.22(m, 2H), 7.59(d, 2H), 7.79(m, 2H), 8.36(m, 1H), 12.71(m, 1H)* |

TABLE-continued

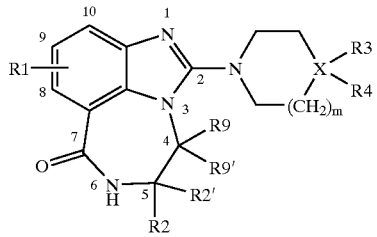

(I) in which R2' = R9' = H

| No. | R1 | R2 | R9 | R3 | R4 | X | m | Salt | NMR |
|---|---|---|---|---|---|---|---|---|---|
| 30 | H | H | H | — | cyclohexyl-CH2- | N | 1 | — | 1.08(m, 1H), 1.21(m, 4H), 1.57(m, 1H), 1.75(m, 4H), 2.29(m, 1H), 2.66(m, 4H), 3.23(m, 4H), 3.47(m, 2H), 4.12(m, 2H), 7.15(t, 1H), 7.57(m, 2H), 8.32(m, 1H)** |
| 31 | H | H | H | — | tetrahydroisoquinolinyl-butyl | N | 1 | — | 1.72(m, 2H), 2.40(m, 2H), 2.55(m, 4H), 2.64(m, 2H), 2.79(m, 2H), 3.27(m, 4H), 3.48(m, 2H), 3.53(s, 2H), 4.13(m, 2H), 7.06(m, 4H), 7.16(t, 1H), 7.58(m, 2H), 8.33(m, 1H), CH2 missing under DMSO peak at 2.48 ppm** |
| 32 | 10-CH$_3$ | H | H | — | 4-F-C6H4-CH2- | N | 1 | — | 2.5(s, 3H), 3.26(m, 4H), 3.39(m, 4H), 3.48(m, 2H), 4.18(m, 2H), 7.03(m, 3H), 7.08(m, 2H), 7.53(d, 1H), 8.25(m, 1H)** |
| 33 | 10-CH$_3$ | H | H | — | cyclohexyl-CH2- | N | 1 | — | 1.09(m, 1H), 1.22(m, 4H), 1.58(m, 1H), 1.76(m, 4H), 2.29(m, 1H), 2.48(s, 3H), 2.64(m, 4H), 3.22(m, 4H), 3.45(m, 2H), 4.10(m, 2H), 6.98(d, 1H), 7.49(d, 1H), 8.22(m, 1H)** |
| 34 | 8-CH$_3$ | H | H | — | 4-F-C6H4-CH2- | N | 1 | — | 2.51(s, 3H), 3.24(m, 4H), 3.41(m, 6H), 4.09(m, 2H), 7.04(m, 5H), 7.41(d, 1H), 8.34(m, 1H) |
| 35 | 9-CH$_3$ | H | H | — | 4-F-C6H4-CH2- | N | 1 | — | 2.39(s, 3H), 3.25(m, 4H), 3.40(m, 4H), 3.48(m, 2H), 4.16(m, 2H), 7.05(m, 4H), 7.42(m, 2H), 8.30(m, 1H) |
| 36 | H | H | Pr | — | 4-F-C6H4-CH2- | N | 1 | — | 0.91(t, 3H), 1.27(m, 1H), 1.45(m, 1H), 1.53(m, 1H), 1.68(m, 1H), 3.26(m, 5H), 3.39(m, 2H), 3.57(m, 2H), 4.63(m, 1H), 7.05(m, 4H), 7.22(t, 1H), 7.68(d, 1H), 7.79(d, 1H), 8.18(m, 1H) |
| 37 | H | H | H | — | —CO—CH$_2$—N(CH$_3$)$_2$ | N | 1 | — | 2.19(s, 6H), 3.11(s, 2H), 3.23(m, 2H), 3.27(m, 2H), 3.49(m, 2H), 3.63(m, 2H), 3.72(m, 2H), 4.17(m, 2H), 7.18(t, 1H), 7.60(m, 2H), 8.34(m, 1H) |
| 38 | H | H | H | — | 4-HO-C6H4-CH2- | N | 1 | — | 3.14(m, 4H), 3.39(m, 4H), 3.50(m, 2H), 4.18(m, 2H), 6.67(d, 2H), 6.85(d, 2H), 7.18(t, 1H), 7.60(d, 2H), 8.34(m, 1H), 8.67(s, 1H)** |

The compounds of the invention were subjected to pharmacological tests to determine their inhibitory effect on PARP or poly(ADP-ribose)polymerase. The compounds of the invention were subjected to the following test:

Effects of the Compounds on the Enzymatic Activity of PARP

Recombinant human PARP-1 (hPARP-1) is produced by Sf9 cells using a baculovirus expression system (Giner et al., Gene (1992), 114, 279–283). The enzyme is partially purified from the cell extract obtained after precipitation with 70% ammonium sulphate. The hPARP-1 solution obtained is capable of generating 0.5–0.7 nmol of nicotinamide from NAD+ under the standard test conditions described below. The test compounds are dissolved in incubation medium containing 50 mM of tris-HCl, 10 mM of MgCl$_2$, 20 μM of zinc acetate, 1.5 mM of dithiothreitol, 0.2 μg of histone and 0.1 μg of oligonucleotide (GGAATTCC) per 100 μl, in the presence of partially purified hPARP-1 buffered to pH 8. The enzymatic reaction is initiated by addition of NAD+ (0.2 mM) and continued at room temperature for 20 minutes. The reaction is stopped by addition of $HClO_4$ (1.2 M) at 4° C. After centrifugation, the supernatants are analysed by HPLC (Shandon Ultrabase C8 column). Isocratic elution is performed with a phosphate buffer (0.1 M) of pH 4.5 containing 6% acetonitrile, injected at 1.25 ml/min for 6 minutes. The nicotinamide formed is detected by measuring the UV absorbance of the eluate at 265 nm and quantified relative to the peak formed with a nicotinamide external standard (2 nmol). The residual hPARP-1 activity measured in the presence of variable concentrations of compounds of the invention is compared with that obtained in their absence. All the measurements are performed at least in duplicate and the $IC_{50}$ values are calculated using the effect-dose sigmoid equation.

The compounds that are most active in this test are characterized by $IC_{50}$ values of between 5 and 500 nM.

Moreover, the compounds in accordance with the invention that are most active towards PARP-2 are also characterized by $IC_{50}$ values of between 5 and 500 nM.

It is thus seen that the compounds of the invention have selective inhibitory activity on PARP, especially on PARP-1 and PARP-2.

The compounds of the invention may thus be used for the preparation of medicinal products, in particular PARP-inhibiting medicinal products. These medicinal products find their application in therapy, especially in the prevention or treatment of myocardial infarction, cardiac ischemia, cardiac insufficiency, atherosclerosis, restenosis after PTCA or bypass, cerebral ischemia and cerebral infarction, caused by an ischemia, trauma or a thromboembolic accident, neurodegenerative diseases, for instance Parkinson's disease, Alzheimer's disease and Huntington's chorea, acute renal insufficiency, in particular that of ischemic origin or appearing after kidney transplant or heart transplant: treatment of graft rejection and of accelerated graft atherosclerosis, inflammatory pathologies, immunological disorders, rheumatoid diseases, diabetes and pancreatitis, septic shock, acute respiratory distress syndrome, tumours and metastases, autoimmune diseases, AIDS, hepatitis, psoriasis, vasculitis, ulcerative colitis, multiple sclerosis and myasthenia.

Thus, the compounds of formula (I) in accordance with the invention may be used to prepare a medicinal product for treating or preventing disorders in which the enzyme PARP is involved.

Finally, the present invention also relates to pharmaceutical compositions containing, as active principle, a compound of formula (I) according to the invention. These pharmaceutical compositions contain an effective dose of a compound according to the invention, or a pharmaceutically acceptable salt thereof, and one or more suitable pharmaceutical excipients. The said excipients are chosen according to the pharmaceutical form and the desired mode of administration.

In the pharmaceutical compositions of the present invention for oral, sublingual, subcutaneous, intramuscular, intravenous, topical, intratracheal, intranasal, transdermal or rectal administration, the active principle of formula (I) above, or the possible salt or hydrate thereof, may be administered in a unit administration form, mixed with standard pharmaceutical excipients, to animals and humans for the prophylaxis or treatment of the above disorders or diseases. The unit forms of administration that are suitable comprise oral forms such as tablets, gel capsules, powders, granules and oral solutions or suspensions, sublinual, buccal, intratracheal and intranasal administration forms, subcutaneous, intramuscular or intravenous administration forms and rectal administration forms. For topical application, the compounds according to the invention may be used in creams, ointments or lotions.

The dose of active principle administered per day may be from 0.1 to 1 000 mg/kg orally, parenterally or rectally. There may be special cases in which higher or lower doses are appropriate, and such doses are not outside the context of the invention. According to the usual practice, the dose which is appropriate to each patient is determined by the doctor according to the mode of administration, the weight and the response of the said patient.

When a solid composition in the form of tablets is prepared, the main active ingredient is mixed with a pharmaceutical excipient, such as gelatin, starch, lactose, magnesium stearate, talc, gum arabic or the like. The tablets may be coated with sucrose, a cellulose derivative or other materials. The tablets may be made by various techniques, such as direct tabletting, dry granulation, wet granulation or hot melting.

A preparation in the form of gel capsules is obtained by mixing the active ingredient with a diluent and pouring the mixture obtained into soft or hard gel capsules.

For a parenteral administration, aqueous suspensions, isotonic saline solutions or sterile injectable solutions which contain pharmacologically acceptable dispersants and/or wetting agents, for example propylene glycol or butylene glycol, may be used.

According to another of its aspects, the present invention also relates to a method for treating the pathologies indicated above, which comprises the administration to a patient of an effective dose of a compound of formula (I) according to the invention, or a pharmaceutically acceptable salt thereof.

What is claimed is:

1. A compound of formula (I)

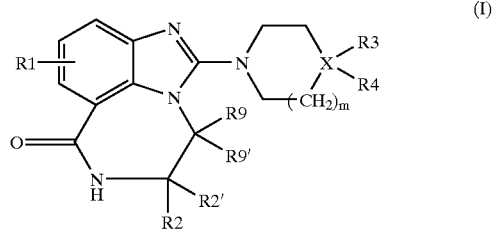

(I)

in which

R1 represents a hydrogen atom, a (C1–C4)alkyl group, a halogen atom, a nitro group or a (C1–C4)alkoxy group, R2, R2', R9 and R9' represent, independently of each other, a hydrogen atom or a (C1–C4)alkyl group, X represents a nitrogen atom or a carbon atom, m is equal to 1 or 2, and when X represents a nitrogen atom:

R3 represents a hydrogen atom or a (C1–C4)alkyl group, or alternatively, R3 is not present, R4 represents
  a hydrogen atom, or
  a (C1–C6)alkyl group, or
  a (C3–C7)cycloalkyl group, or
  a 4-piperidyl group optionally substituted on a carbon atom or on the nitrogen atom with a (C1–C4)alkyl group, or
  a group —$(CH_2)_p$—NR5R6, —$(CH_2)_p$—CONR5R6 or —CO—$(CH_2)_p$—NR5R6, in which p may range from 0 to 4 and in which
  R5 and R6 represent, independently of each other, a hydrogen atom or a (C1–C4)alkyl group, or
  a group —$(CH_2)_p$-phenyl, in which p may range from 0 to 4 and in which the phenyl radical is optionally substituted with one to three groups chosen, independently of each other, from: a (C1–C4)alkyl group, a nitro group, a hydroxyl group, an amino group, a halogen atom, a trifluoromethyl group, a (C1–C4)alkoxy group, a (C1–C4)alkylamino group, a (C1–C4)dialkylamino group, a —NHCHO group, a group —NHCOR and a group —NHSO$_2$R, in which R represents a (C1–C4)alkoxy group or a (C1–C4)alkyl group, wherein the (C1–C4)alkyl group is optionally substituted with a dimethylamino group, or a group —(CH$_2$)$_p$-morpholinyl, —(CH$_2$)$_p$-pyrrolidinyl or —(CH$_2$)$_p$-tetrahydroisoquinoline, in which p may range from 0 to 4, or a group —(CH$_2$)$_p$-heteroaryl, in which p may range from 0 to 4 and in which the heteroaryl group is chosen from pyridyl, aminopyridyl, pyridyl N-oxide, pyrimidinyl, pyrazinyl, pyridazinyl, imidazolyl and pyrazolyl groups, wherein said heteroaryl group is optionally substituted on a carbon atom, on a nitrogen atom, or on both a carbon atom and a nitrogen atom, with one to three groups chosen from a (C1–C4)alkyl group and a phenyl group, wherein the phenyl group is optionally substituted with one to three groups chosen from halogen atoms and (C1–C4)alkyl groups, or a heteroarylcarbonyl group, wherein the heteroaryl part of the heteroarylcarbonyl group is chosen from furyl, pyridyl, pyrimidyl, pyrazinyl, pyridazinyl and imidazolyl groups, or a phenylcarbonyl group, wherein the phenyl part of the phenylcarbonyl group is optionally substituted with a halogen atom, or a (C1–C6)alkylcarbonyl group, or a group —(CH$_2$)$_p$—COOR' in which p may range from 0 to 4 and in which R' represents a hydrogen atom or a (C1–C6)alkyl group, or a phenylsulphonyl group, optionally substituted on the phenyl radical with a halogen atom, a trifluoromethyl group, a (C1–C4)alkyl group, a nitro group or a (C1–C4)alkoxy group;

and when X represents a carbon atom:

R3 represents a hydrogen atom, a group —NR5R6, a group —NHCOR7, a group —CONHR5, a group —COR7, an —NHCONH$_2$ group, an —OH group or a —CH$_2$OH group, R4 represents:

a hydrogen atom, or a group —(CH$_2$)$_p$-phenyl, in which p may range from 0 to 4 and in which the phenyl radical is optionally substituted with one to three groups chosen, independently of each other, from: a (C1–C4)alkyl group, a nitro group, a hydroxyl group, an amino group, a halogen atom, a trifluoromethyl group, a (C1–C4)alkoxy group, a (C1–C4)alkylamino group, a (C1–C4)dialkylamino group, an —NHCHO group, a group —NHCOR and a group —NHSO$_2$R, in which R represents a (C1–C4)alkoxy group or a (C1–C4)alkyl group, wherein the (C1–C4)alkyl group is optionally substituted with a dimethylamino group, or a group —(CH$_2$)$_p$-heteroaryl, in which p may range from 0 to 4 and in which the heteroaryl group is chosen from pyridyl, aminopyridyl, pyridyl N-oxide, pyrimidinyl, pyrazinyl, pyridazinyl, imidazolyl and pyrazolyl groups, wherein said heteroaryl group is optionally substituted on a carbon atom, on a nitrogen atom, or on both a carbon atom and a nitrogen atom, with one to three groups chosen from a (C1–C4)alkyl group and a phenyl group, wherein the phenyl group is optionally substituted with one to three groups chosen from halogen atoms and (C1–C4)alkyl groups, or a group —(CH$_2$)$_t$NR7R8, in which t is equal to 0 or 1, R5 and R6 represent, independently of each other, a hydrogen atom or a (C1–C4)alkyl group, R7 and R8 represent, independently of each other, a (C1–C4)alkyl or (C1–C4)alkoxy group, or R7 and R8 together form a 5- to 7-membered saturated ring optionally having an additional nitrogen atom, wherein the ring is optionally substituted with a (C1–C4)alkyl group on a carbon atom or a nitrogen atom, including on the nitrogen atom to which the groups R7 and R8 are attached, or an enantiomer or diastereolsomer of a compound of formula I, or a mixture thereof, including a racemic mixture, or a base or addition salt of a compound of formula I with a pharmaceutically acceptable acid.

2. A compound according to claim 1, wherein

R1, R2 and R9 represent, independently of each other, a hydrogen atom or a (C1–C4)alkyl group, R2' and R9' each represents a hydrogen atom, X represents a nitrogen atom, m is equal to 1 or 2, R3 represents a (C1–C4)alkyl group, or alternatively, R3 is not present, R4 represents a hydrogen atom, or a (C1–C6)alkyl group, or a (C3–C7)cycloalkyl group, or a 4-piperidyl group, optionally substituted on a carbon atom or on the nitrogen atom with a (C1–C4)alkyl group, or a group —(CH$_2$)$_p$—NR5R6, —(CH$_2$)$_p$—CONR5R6 or —CO—(CH$_2$)$_p$—NR5R6, in which p may range from 0 to 4 and in which R5 and R6 represent, independently of each other, a hydrogen atom or a (C1–C4)alkyl group, or a group —(CH$_2$)$_p$-phenyl, in which p may range from 0 to 4 and in which the phenyl radical is optionally substituted with one to three groups chosen, independently of each other, from a nitro group, a halogen atom and a trifluoromethyl group, or a group —(CH$_2$)$_p$-morpholinyl, —(CH$_2$)$_p$-pyrrolidinyl or —(CH$_2$)$_p$-tetrahydroisoquinoline, in which p may range from 0 to 4, or a group —(CH$_2$)$_p$-pyrazolyl, in which p may range from 0 to 4 and in which the pyrazolyl group is optionally substituted on a carbon atom, on a nitrogen atom, or on both a carbon atom and a nitrogen atom, with one to three groups chosen from a (C1–C4)alkyl group and a phenyl group, or a group —(CH$_2$)$_p$-pyridyl, in which p may range from 0 to 4, or a heteroarylcarbonyl group, wherein the heteroaryl part of the heteroarylcarbonyl group is chosen from a furyl group or a pyridyl group, or a phenylcarbonyl group, wherein the phenyl part of the heteroarylcarbonyl group is optionally substituted with a halogen atom, or a (C1–C6)alkylcarbonyl group, or a group —(CH$_2$)$_p$—COOR' in which p may range from 0 to 4 and in which R' represents a (C1–C6)alkyl group, or a phenylsulphonyl group;

or where

R1, R2' and R9', each represents a hydrogen atom,

R2 and R9 represent, independently of each other, a hydrogen atom or a (C1–C4)alkyl group, X represents a carbon atom, m is equal to 1, R3 represents a hydrogen atom, a group —NR5R6, a group —NHCOR7, a group —CONHR5, a group —COR7, an —NHCONH$_2$ group, an —OH group or a —CH$_2$OH group, R4 represents
- a hydrogen atom, or
- a phenyl group, or
- a heteroaryl group chosen from:
  - an imidazolyl group, optionally substituted with a (C1–C4)alkyl group,
  - a pyridyl group, optionally substituted on a nitrogen atom or on a carbon atom with a phenyl group, wherein the phenyl group is optionally substituted with one to three groups chosen from halogen atoms and (C1–C4)alkyl groups, and
  - a pyrazolyl group, optionally substituted on a nitrogen atom or on a carbon atom with a phenyl group, wherein the phenyl group is optionally substituted with one to three groups chosen from halogen atoms and (C1–C4)alkyl groups, or
- a group —NR7R8, R5 and R6 represent, independently of each other, a hydrogen atom or a (C1–C4)alkyl group, R7 and R8 represent, independently of each other, a (C1–C4)alkyl or (C1–C4)alkoxy group, or R7 and R8 together form a saturated 5- to 7-membered ring optionally having an additional nitrogen atom,
  wherein the ring is optionally substituted with a (C1–C4)alkyl group on a carbon atom or on a nitrogen atom, including on the nitrogen atom to which the groups R7 and R8 are attached.

3. A compound according to claim 1, wherein

R1, R2 and R9 represent, independently of each other, a hydrogen atom or a (C1–C4)alkyl group, R2' and R9', each represents a hydrogen atom, X represents a nitrogen atom, m is equal to 1 or 2, R3 represents a (C1–C4)alkyl group, or alternatively, R3 is not present, R4 represents
- a hydrogen atom, or
- a (C1–C4)alkyl group, or
- a (C3–C7)cycloalkyl group, or
- a 4-piperidyl group optionally substituted on the nitrogen atom with a (C1–C4)alkyl group, or
- a group —(CH$_2$)$_p$—NR5R6, —(CH$_2$)$_p$—CONR5R6 or —CO—(CH$_2$)$_p$—NR5R6, in which p is between 1 and 3 and in which R5 and R6 represent, independently of each other, (C1–C4)alkyl groups, or
- a group —(CH$_2$)$_p$-phenyl, in which p may range from 0 to 4 and in which the phenyl radical is optionally substituted with one to three groups chosen, independently of each other, from a nitro group, a halogen atom and a trifluoromethyl group, or
- a group —(CH$_2$)$_p$-morpholinyl, —(CH$_2$)$_p$-pyrrolidinyl or —(CH$_2$)$_p$-tetrahydroisoquinoline, in which p is equal to 2 or 3, or
- a group —(CH$_2$)$_p$-pyrazolyl, in which p may range from 0 to 4 and in which the pyrazole group may be substituted on a carbon atom, on a nitrogen atom, or on both a carbon atom and a nitrogen atom, with one to three groups chosen from a (C1–C4)alkyl group and a phenyl group, or
- a group —(CH$_2$)$_p$-heteroaryl, in which p is equal to 0 or 1 and in which the heteroaryl group is a 4-pyridyl or a 2-pyridyl group, or
- a (C1–C4)alkylcarbonyl group, or
- a group —COOR' in which R' represents a (C1–C4) alkyl group;

or where

R1, R2' and R9', each represents a hydrogen atom,

R2 and R9 represent, independently of each other, a hydrogen atom or a (C1–C4)alkyl group, X represents a carbon atom, m is equal to 1, R3 represents a hydrogen atom, a —NH$_2$ group or a group —NHCOR7, R4 represents
- a phenyl group, or
- a heteroaryl group chosen from:
  - an imidazolyl group optionally substituted with a (C1–C4)alkyl group, and
  - a pyrazolyl group optionally substituted, on a carbon atom, with a phenyl group, wherein the phenyl group is optionally substituted with one to three groups chosen from halogen atoms and (C1–C4) alkyl groups, or
- a group —NR7R8, in which R7 and R8 represent, independently of each other, a (C1–C4)alkyl or (C1–C4)alkoxy group, or R7 and R8 together form a saturated 5- to 7-membered ring,
  wherein the ring is optionally substituted with a (C1–C4)alkyl group on a carbon atom or on a nitrogen atom, including on the nitrogen atom to which the groups R7 and R8 are attached.

4. A compound according to claim 1, wherein when X represents a nitrogen atom:

R4 represents:
- a 4-piperidyl group substituted, on a carbon atom or on the nitrogen atom, with a (C1–C4)alkyl group, or
- a group —(CH$_2$)$_p$—NR5R6 or —(CH$_2$)$_p$—CONR5R6, in which p may range from 1 to 4 and in which
  R5 and R6 represent, independently of each other, a (C1–C4)alkyl group, or
- a group —CO—(CH$_2$)$_p$—NR5R6, in which p may range from 0 to 4 and in which
  R5 and R6 represent, independently of each other, a hydrogen atom or a (C1–C4)alkyl group; or
- a group —(CH$_2$)$_p$-phenyl, in which p may range from 1 to 4 and in which the phenyl radical is optionally substituted with one to three groups chosen, independently of each other, from: a (C1–C4)alkyl group, a nitro group, a hydroxyl group, an amino group, a halogen atom, a trifluoromethyl group, a (C1–C4)alkoxy group, a (C1–C4)alkylamino group, a (C1–C4)dialkylamino group, an —NHCHO group and a group —NHCOR, in which
  R represents a (C1–C4)alkoxy group or a (C1–C4) alkyl group, wherein the (C1–C4)alkyl group is optionally substituted with a dimethylamino group, or
- a group —(CH$_2$)$_p$-morpholinyl, —(CH$_2$)$_p$-pyrrolidinyl or —(CH$_2$)$_p$-tetrahydroisoquinoline, in which p may range from 1 to 4, or
- a group —(CH$_2$)$_p$-heteroaryl, in which p may range from 1 to 4 and in which the heteroaryl group is chosen from pyridyl, aminopyridyl, pyrimidinyl, pyrazinyl, pyridazinyl, imidazolyl and pyrazolyl groups, wherein said heteroaryl group is optionally substituted on a carbon atom, on a nitrogen atom, or on both a carbon atom and a nitrogen atom, with one to three groups chosen from a (C1–C4)alkyl group or a phenyl group, or a heteroarylcarbonyl group, wherein the heteroaryl part of the heteroarylcarbonyl group is chosen from furyl, pyridyl, pyrimidyl, pyrazinyl, pyridazinyl and imidazolyl groups, or a phenylcarbonyl group, wherein the phenyl part of the phenylcarbonyl group is optionally substituted with a halogen atom, or a (C1–C6)alkylcarbonyl group, or a group —(CH$_2$)$_p$—COOR' in which p may range from 0 to 4 and in which R' represents a hydrogen atom or a (C1–C6)alkyl group, or a phenylsulphonyl group optionally substituted on the phenyl radical with a halogen atom, a trifluoromethyl group, a (C1–C4)alkyl group, a nitro group or a (C1–C4)alkoxy group, or a group —CO—(CH$_2$)$_p$—NR5R6, in which p may range from 0 to 4 and in which
R5 and R6 represent, independently of each other, a hydrogen atom or a (C1–C4)alkyl group; or when X represents a carbon atom:
R3 represents
a group —NR5R6, in which R5 and R6 represent, independently of each other, a (C1–C4)alkyl group; or
a group —NHCOR7, in which R7 represents a (C1–C4)alkoxy group; or
a group —CONHR5, in which R5 represents a hydrogen atom or a (C1–C4)alkyl group; or
a group —COR7, in which R7 represents a (C1–C4)alkyl or (C1–C4)alkoxy group; or
a —NHCO NH$_2$ group, or, alternatively, when X represents a carbon atom:
R4 represents:
a phenyl group substituted with one to three groups chosen, independently of each other, from: a (C1–C4)alkyl group and a trifluoromethyl group, or
an imidazolyl group substituted with a (C1–C4)alkyl group, or
a pyrazolyl group substituted, on a nitrogen atom or on a carbon atom, with a phenyl group wherein the phenyl group is optionally substituted with one to three groups chosen from halogen atoms and (C1–C4)alkyl groups, or
a group —CH$_2$—NR7R8, or
a group —NR7R8,
in which R7 and R8 represent, independently of each other, a (C1–C4)alkyl group or R7 and R8 together form a saturated 5- to 7-membered ring optionally having an additional nitrogen atom, wherein the ring is optionally substituted with a (C1–C4)alkyl group on a carbon atom or on a nitrogen atom, including on the nitrogen atom to which the groups R7 and R8 are attached.

5. A process for preparing a compound according to claim 1, comprising reacting a compound of formula (II)

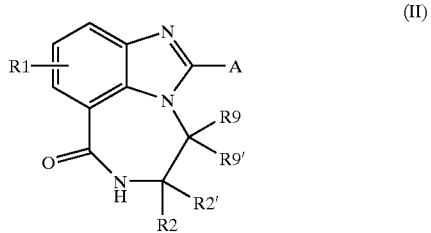

(II)

in which A represents a leaving group, with an amine of formula (III)

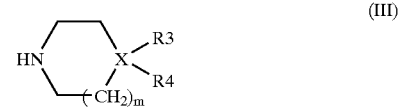

(III)

to obtain a compound of formula (I), and optionally reacting the compound of formula (I) with a pharmaceutically acceptable acid to form an addition salt of a compound of formula (I).

6. A pharmaceutical composition, comprising at least one compound as claimed in claim 1, and one or more suitable pharmaceutical excipients.

7. A compound as claimed in claim 1, wherein, when X represents a carbon atom and when R4 represents a —NR7R8 group, R7 and R8 together form a saturated 5- to 7-membered ring chosen from a 1-piperidyl group, a 1-pyrrolidinyl group and a 1-piperazinyl group, and
wherein the ring is optionally substituted with a (C1–C4) alkyl group on a carbon atom or a nitrogen atom, including on the nitrogen atom to which the groups R7 and R8 are attached.

8. A compound as claimed in claim 2, wherein, when X represents a carbon atom and when R4 represents a —NR7R8 group, R7 and R8 together form a saturated 5-to 7-membered ring chosen from a 1-piperidyl group, a 1-pyrrolidinyl group and a 1-piperazinyl group, and
wherein the ring is optionally substituted with a (C1–C4) alkyl group on a carbon atom or a nitrogen atom, including on the nitrogen atom to which the groups R7 and R8 are attached.

9. A compound as claimed in claim 3, wherein, when X represents a carbon atom and when R4 represents a —NR7R8 group, R7 and R8 together form a 1-piperidyl group, and
wherein the piperidyl ring is optionally substituted with a (C1–C4)alkyl group on a carbon atom or a nitrogen atom, including on the nitrogen atom to which the groups R7 and R8 are attached.

10. A compound as claimed in claim 4, wherein, when X represents a carbon atom and when R4 represents a —NR7R8 group, R7 and R8 together form a saturated 5- to 7-membered ring chosen from a 1-piperidyl group, a 1-pyrrolidinyl group and a 1-piperazinyl group, and
wherein the ring is optionally substituted with a (C1–C4) alkyl group on a carbon atom or a nitrogen atom, including on the nitrogen atom to which the groups R7 and R8 are attached.

11. A process according to claim 5, wherein the reaction of a compound of formula (II) with a compound of formula (III) takes place in a solvent chosen from an alcohol, an ether, dimethylformamide and a hydrocarbon.

12. A process according to claim 5, wherein the reaction of a compound of formula (II) with a compound of formula (III) takes place in the presence of a base, in the presence of alkali metal halide, or in the presence of palladium-based or nickel-based catalysts.

13. A process according to claim 5, wherein the leaving group A is a halogen.

* * * * *

UNITED STATES PATENT AND TRADEMARK OFFICE
CERTIFICATE OF CORRECTION

PATENT NO.    : 6,979,683 B2
DATED         : December 27, 2005
INVENTOR(S)   : Francis Barth et al.

It is certified that error appears in the above-identified patent and that said Letters Patent is hereby corrected as shown below:

Column 28,
Line 18, "diastereolsomer" should read -- diastereoisomer --.

Column 31,
Line 33, "-NHCO $NH_2$" should read -- -$NHCONH_2$ --.

Column 32,
Line 28, "5-to" should read -- 5- to --.

Signed and Sealed this

Fourteenth Day of February, 2006

JON W. DUDAS
*Director of the United States Patent and Trademark Office*